(12) United States Patent
Haught et al.

(10) Patent No.: US 9,937,115 B2
(45) Date of Patent: Apr. 10, 2018

(54) ORAL CARE COMPOSITIONS WITH IMPROVED FLAVOR

(75) Inventors: John Christian Haught, West Chester, OH (US); Christine Marie Cahen, Bonn (DE); Koti Tatachar Sreekishna, Mason, OH (US); Wenzhu Zhao, Mason, OH (US); Yakang Lin, Liberty Township, OH (US); Cathy Renee Schinaman, West Harrison, IN (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 403 days.

(21) Appl. No.: 13/248,308

(22) Filed: Sep. 29, 2011

(65) Prior Publication Data

US 2012/0082628 A1 Apr. 5, 2012

Related U.S. Application Data

(60) Provisional application No. 61/388,752, filed on Oct. 1, 2010.

(51) Int. Cl.

| | | |
|---|---|---|
| *A61K 8/58* | (2006.01) | |
| *A61K 8/37* | (2006.01) | |
| *A61K 8/49* | (2006.01) | |
| *A61K 8/60* | (2006.01) | |
| *A61Q 11/00* | (2006.01) | |

(52) U.S. Cl.
CPC .............. *A61K 8/37* (2013.01); *A61Q 11/00* (2013.01)

(58) Field of Classification Search
CPC ........... A61K 8/37; A61K 8/347; A61Q 11/00
See application file for complete search history.

(56) References Cited

U.S. PATENT DOCUMENTS

| | | | | |
|---|---|---|---|---|
| 5,628,986 | A * | 5/1997 | Sanker et al. | 424/49 |
| 5,900,230 | A * | 5/1999 | Cutler | 424/49 |
| 6,899,901 | B2 * | 5/2005 | Nakatsu et al. | 424/725 |
| 7,851,000 | B2 | 12/2010 | Boghani et al. | |
| 7,851,006 | B2 | 12/2010 | Bingley et al. | |
| 7,879,376 | B2 | 2/2011 | Boghani et al. | |
| 2002/0119231 | A1 * | 8/2002 | Kumamoto et al. | 426/534 |
| 2003/0007937 | A1 * | 1/2003 | Lawlor | A23G 3/346 424/57 |
| 2007/0036733 | A1 * | 2/2007 | Spence | A23L 1/22066 424/48 |
| 2008/0317923 | A1 * | 12/2008 | Ley et al. | 426/535 |
| 2009/0004360 | A1 | 1/2009 | Bingley et al. | |
| 2009/0110648 | A1 | 4/2009 | Cedeno | |
| 2010/0278991 | A1 * | 11/2010 | Haught | A61K 8/19 426/532 |

FOREIGN PATENT DOCUMENTS

| | | | |
|---|---|---|---|
| JP | 2004-018431 | * | 1/2004 |
| WO | WO2008/105652 | * | 9/2008 |

OTHER PUBLICATIONS

Derivative definition at medical-dictionary.thefree dictionary.com/derivative (retrieved from the internet Jul. 8, 2013).*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Baraldi, Pier Giovanni et al., "Transient Receptor potential Ankyrin 1 (TRPA1) Channel as Emerging Target for Novel Analgesics and Anti-Inflammatory Agents", Journal of Medicinal Chemistry Perspective, DOI: 10.1021/jm100062h.

* cited by examiner

*Primary Examiner* — Dennis Heyer
(74) *Attorney, Agent, or Firm* — James E. Oehlenschlager

(57) ABSTRACT

Oral care compositions having improved taste, said compositions comprising: a carrier material; from about 0.001 to about 10%, by weight of the composition, of an oral care component selected from metal salts, antimicrobial agents, bad breath reduction agents, bleaching agents, surfactants, or a combination thereof; and from about 0.0001 to about 1%, by weight of the composition, of a TRPA1 agonist selected from vanillin esters; benzoate esters; hydroxybenzoate derivatives; methoxy benzoate derivatives; hydroxybutanedioate derivatives; benzamidobenzoate derivatives; methylpropanoate derivatives; phenyl acetate derivatives; hex-3-enoate derivatives; 2-(furan-2-ylmethylsulfanyl)-3-methylpyrazine; phenylmethoxymethylbenzene; (2R)-2-azaniumyl-3-[(2R)-2-azaniumyl-3-oxido-3-oxopropyl]disulfanylpropanoate; (3E)-2-hydroxy-4,8-dimethylnona-3,7-dienal; (2R)-2-azaniumyl-3-[(2S)-2-azaniumyl-3-oxido-3-oxopropyl]disulfanylpropanoate; (3Z)-3-butylidene-2-benzofuran-1-one; 3-methyl-N-(3-methylbutyl)butan-1-imine; 2-(furan-2-ylmethyldisulfanylmethyl)furan; and combinations thereof. Uses thereof and methods of improving the taste of an oral care composition.

14 Claims, No Drawings

US 9,937,115 B2

ORAL CARE COMPOSITIONS WITH IMPROVED FLAVOR

CROSS REFERENCE TO RELATED APPLICATION

This application claims the benefit of U.S. Application No. 61/388,752, filed Oct. 1, 2010, the substance of which is incorporated by reference in its entirety herein.

FIELD OF THE INVENTION

The present invention relates to oral care compositions and methods of improving the taste thereof.

BACKGROUND OF THE INVENTION

Traditionally, much effort has been expended to improve the taste, color, odor or clarity of oral care compositions such as dentifrice (toothpaste), mouth rinse, and the like. Because of the nature of such compositions, the taste of a product may often be of more importance to consumers than the actual efficacy. Since many efficacious oral care components have undesirable taste, color, odor or clarity, efforts to improve these characteristics are common in the art.

It is highly desirable that consumer products for use in cleaning and care of the oral cavity impart a fresh and clean feeling as this provides consumers with a signal of continuing freshness and cleanliness. In addition to the feeling of cleanliness, consumers also want to experience the benefits of oral care actives like anti-microbial agents, for example, through their oral care regimen. The ability to formulate a consumer acceptable oral care composition, however, raises challenges as many of the components used to impart a flavor, deliver a benefit, or that are part of the base for the oral care composition add unwanted tastes and/or sensations along with the targeted benefit for which they are added. Thus, formulating oral care compositions can be a balancing act between acceptable flavor and acceptable benefits.

The sensations of bitter and sweet tastes are initiated by the interaction of sapid molecules ("tastants") with G protein-coupled receptors (GPCRs) in the apical membranes of taste receptor cells (TRCs). TRCs are specialized epithelial cells with many neuronal properties including the ability to depolarize and form synapses. TRCs are typically clustered in groups of ~100 within taste buds. The apical surface of TRCs, which makes contact with the oral cavity, is rich in convoluted microvilli containing GPCRs, ion channels, and other transduction elements. The basolateral aspect of TRCs contains ion channels and synapses with afferent taste nerves. Most sweeteners are small molecular mass compounds but a few sweet-tasting proteins have been described. Low molecular mass sweeteners and sweet-tasting proteins interact with the same receptor, as shown by recent, direct experiments: at least two of the well-characterized sweet proteins, i.e. brazzein and thaumatin, elicit a response in the human T1R2-T1R3 receptor, similar to that elicited by small molecular mass sweeteners. The sweet taste receptor is a heterodimer of two G protein coupled receptors, T1R2 and T1R3. Heteromeric T1R2:T1R3 taste receptors respond to sweet-tasting compounds such as sugars, high-potency sweeteners, and some D amino acids, whereas T1R1:T1R3 heteromers comprise a umami taste receptor sensitive to L amino acids [12 and 16]. Domains of human T1R2 and T1R3 are sufficient to confer sensitivity to some noncaloric sweeteners and sweet-tasting proteins to which rodents are indifferent, but it remains unknown which of these receptor subunits participates in the binding of most sweet stimuli, including sugars. G protein-coupled receptors mediate many other physiological functions, such as endocrine function, exocrine function, heart rate, lipolysis, and carbohydrate metabolism. The biochemical analysis and molecular cloning of a number of such receptors has revealed many basic principles regarding the function of these receptors. For example, U.S. Pat. No. 5,691,188 describes how upon a ligand binding to a GPCR, the receptor undergoes a conformational change leading to activation of a heterotrimeric G protein by promoting the displacement of bound GDP by GTP on the surface of the Gα subunit and subsequent dissociation of the Gα subunit from the Gβ and Gγ subunits. The free Gα subunits and Gβγ complexes activate downstream elements of a variety of signal transduction pathways.

Compositions taken into the oral cavity are first detected by taste receptors/channels and trigeminal neurons. This information is transmitted to the brain via trigeminal neurons and taste cells. Taste sensation is finally perceived in the brain as sweet, bitter, sour, salty, or savory. TRPA1 is a known, nonselective cation channel that belongs to the superfamily of Transient Receptor Potential (TRP) ion channels. The TRPA1 receptor acts to tell the human body that a substance in the oral cavity is unpleasant and should be expelled by conveying a pungent, bitter, unpleasant taste. A summary of the TRPA1 channel (as an emerging target for new analgesics and anti-inflammatory agents) with several of the TRPA1 agonists noted, is found in the article *Transient Receptor Potential Ankyrin* 1 (*TRPA*1) *Channel as Emerging Target for Novel Analgesics and Anti-Inflammatory Agents*, by Pier Giovanni Baraldi, et al, J. Med. Chem., Submitted Jan. 15, 2010. Of note, TRPA1 agonists such as citriol, eugenol, thymol, cinnamaldehyde (contained in cinnamon), eugenol, citral, geraniol, eugenol acetate, citral dimethyl acetal, or citral diethyl acetal, and certain flavorings used in oral care compositions typically express pungent, unpleasant tastes in the oral cavity.

However, many TRPA1 agonists are desirable in oral care compositions to provide other benefits. Therefore, there is a need to develop oral care compositions that contain materials that can bind to the TRPA1 receptor and yet provide a neutral or positive taste.

In US Patent Application No. 2008/0124753A1, it was disclosed that a taste profile can be created by dually activating two or more TRP receptors. Although A1 could be one of the receptors activated, the compositions of the '753 application required activation of two or more receptors simultaneously to create an acceptable flavor or taste profile and offered no solution for mitigating unpleasant tastes caused by TRPA1 agonists.

In US Patent Application No. 2008/0050750A1, a method was disclosed in which the TRPA1 receptor was deactivated by antagonistic molecules, in order to block the pungent taste of thymol and other lower alkyl phenols that bind to A1. Their system involved the application of molecules that would shut down an active TRPA1 receptor.

In US Patent Application No. 2009/0175848A1 it was disclosed to modulate (inhibit) TRPA1 ion channel activity by targeting the ion channel TRPM5 and vice versa through the cooperativity mechanism identified therein. More specifically, the US '848 reference disclosed modulating pain, mechanosensation, and taste responses triggered through the ion channels TRPA1 and TRPM5.

In US Patent Application 2008/0242740A1, vanillins and vanillin isobutyrate were generally disclosed as one of a series of compounds that gave rise to a sweet odor impression. The disclosed purpose of US '740 was to enhance the sweetness of chalcones via saliva stimulating agents and materials that give an initial burst of sweetness. No means were provided to remedy off-tasting components.

US Patent Application No. 2008/0317923A1 disclosed suppression of a bitter, astringent impression in the oral cavity via compositions containing saliva stimulating agents, bitterness-masking aroma substances and/or flavorings, of which vanillin esters were not disclosed. Ethyl vanillin isobutyrate was mentioned as a malodor suppressing agent, but was not disclosed as having an effect on off-tasting or bitter substances.

In US Patent Application No. 2009/0004360A1, oral compositions that provide an enhanced perception of an active substance were disclosed. In particular, the compositions included an active substance, such as a sweetener or flavor, and a sweetness modifier. The sweetness modifier was disclosed as increasing the perception of sweetness upon consumption. The compositions could be incorporated into various types of edible orally delivered products, such as beverages, food products, confectionary or chewing gum products. Vanillin isobutyrate was disclosed as a potential sweetness modifier.

Despite the known functionality of the TRPA1 receptor and standard binding materials, a need still exists for an oral care composition containing TRPA1 agonists and yet provide a neutral or positive taste.

SUMMARY OF THE INVENTION

Surprisingly, it has now been found that strong TRPA1 agonists, which are esterified methoxy phenol derivatives, uniquely block bitter and off-tasting A1 agonists from binding to the A1 receptor. Without being limited by theory, vanillin esters and structurally similar compounds act as TRPA1 agonists but still result in a neutral or vanilla taste in the oral cavity. Vanillin derivatives, specifically vanillin esters, provide a means to balance an oral care composition's taste from bitter and poor tasting to a neutral to positive tasting formula. Furthermore, it surprisingly appears that such vanillin esters and structurally similar materials have a relatively strong binding intensity to the TRPA1 receptors and can out-compete with other bitter or poor tasting TRPA1 agonists found in the oral care composition, resulting in an either neutral or pleasant vanilla taste even when other TRPA1 agonists are present in the composition. Without being limited by theory, the vanillin esters "fool" the TRPA1 taste receptor so that it does not convey a message to the human body of an unpleasant taste in the oral cavity.

The present invention is therefore directed to oral care compositions having improved taste, said composition comprising: a carrier material; from about 0.001 to about 10%, by weight of the composition, of an oral care component selected from metal salts, antimicrobial agents, bad breath reduction agents, bleaching agents, surfactants, or a combination thereof; and from about 0.0001 to about 1%, by weight of the composition, of a TRPA1 agonist selected from vanillin esters; benzoate esters; hydroxybenzoate derivatives; methoxy benzoate derivatives; hydroxybutanedioate derivatives; benzamidobenzoate derivatives; methylpropanoate derivatives; phenyl acetate derivatives; hex-3-enoate derivatives; 2-(furan-2-ylmethylsulfanyl)-3-methylpyrazine; phenylmethoxymethylbenzene; (2R)-2-azaniumyl-3-[(2R)-2-azaniumyl-3-oxido-3-oxopropyl]disulfanylpropanoate; (3E)-2-hydroxy-4,8-dimethylnona-3,7-dienal; (2R)-2-azaniumyl-3-[(2S)-2-azaniumyl-3-oxido-3-oxopropyl]disulfanylpropanoate; (3Z)-3-butylidene-2-benzofuran-1-one; 3-methyl-N-(3-methylbutyl)butan-1-imine; 2-(furan-2-ylmethyldisulfanylmethyl)furan; and combinations thereof.

The present invention is further directed to a method for improving taste of an oral care composition, said method comprising the steps of: providing an oral care composition, said composition comprising an oral care component selected from metal salts, antimicrobial agents, bad breath reduction agents, bleaching agents, surfactants, or a combination thereof; and adding to the oral care composition a TRPA1 agonist selected from vanillin esters; benzoate esters; hydroxybenzoate derivatives; methoxy benzoate derivatives; hydroxybutanedioate derivatives; benzamidobenzoate derivatives; methylpropanoate derivatives; phenyl acetate derivatives; hex-3-enoate derivatives; 2-(furan-2-ylmethylsulfanyl)-3-methylpyrazine; phenylmethoxymethylbenzene; (2R)-2-azaniumyl-3-[(2R)-2-azaniumyl-3-oxido-3-oxopropyl]disulfanylpropanoate; (3E)-2-hydroxy-4,8-dimethylnona-3,7-dienal; (2R)-2-azaniumyl-3-[(2S)-2-azaniumyl-3-oxido-3-oxopropyl]disulfanylpropanoate; (3Z)-3-butylidene-2-benzofuran-1-one; 3-methyl-N-(3-methylbutyl)butan-1-imine; 2-(furan-2-ylmethyldisulfanylmethyl)furan; and combinations thereof.

The present invention is further directed to a method for improving the taste of an oral care composition, said method comprising the steps of: providing an oral care composition, said composition a metal salt selected from zinc salts, stannous salts, potassium salts, copper salts, and combinations thereof; and adding to the oral care composition from about 0.001% to about 0.085%, by weight of the composition, of vanillin isobutyrate.

In one embodiment, the present invention relates to such oral care compositions and methods wherein the TRPA1 agonist is selected from vanillin esters, and combinations thereof.

In another embodiment, the present invention relates to oral care compositions and methods as described above wherein the vanillin ester is selected from vanillin isobutyrate, ethyl vanillin isobutyrate, vanillin acetate, vanillin formate, vanillin propionate, vanillin butyrate, vanillin valerate, vanillin caproate, vanillin myrisate, vanillin laurate, vanillin palmitate, vanillin oleate, vanillin stearate, and combinations thereof.

In another embodiment, the present invention relates to oral care compositions and methods as described above wherein the vanillin ester is selected from vanillin acetate, vanillin formate, vanillin propionate, vanillin butyrate, and combinations thereof.

In another embodiment, the present invention relates to oral care compositions as described above wherein the vanillin ester is vanillin propionate.

In another embodiment, the present invention relates to oral care compositions and methods as described above wherein the oral care component is selected from antimicrobial agents, surfactants and combinations thereof.

In another embodiment, the present invention relates to oral care compositions and methods as described above wherein the metal salt is selected from zinc salts, stannous salts, potassium salts, copper salts, and combinations thereof.

In another embodiment, the present invention relates to oral care compositions and methods as described above wherein the stannous salt is selected from stannous fluoride, stannous chloride, stannous iodide, stannous chlorofluoride, stannous actetate, stannous hexafluorozirconate, stannous sulfate, stannous lactate, stannous tartrate, stannous gluconate, stannous citrate, stannous malate, stannous glycinate, stannous pyrophosphate, stannous metaphosphate, stannous oxalate, stannous phosphate, stannous carbonate, and combinations thereof.

In another embodiment, the present invention relates to oral care compositions and methods as described above wherein the zinc salt is selected from zinc fluoride, zinc chloride, zinc iodide, zinc chlorofluoride, zinc actetate, zinc hexafluorozirconate, zinc sulfate, zinc lactate, zinc tartrate, zinc gluconate, zinc citrate, zinc malate, zinc glycinate, zinc pyrophosphate, zinc metaphosphate, zinc oxalate, zinc phosphate, zinc carbonate, and combinations thereof.

In another embodiment, the present invention relates to oral care compositions and methods as described above wherein the potassium salt is selected from potassium nitrate, potassium citrate, potassium oxalate, potassium bicarbonate, potassium acetate, potassium chloride, and combinations thereof.

In another embodiment, the present invention relates to oral care compositions and methods as described above wherein the composition further comprises a sweetener selected from sucralose, REBIANA, NHDC, acesulfame K, or a combination thereof.

In another embodiment, the present invention relates to oral care compositions and methods as described above wherein the composition further comprises from about 0.01% to about 30% of an abrasive.

In another embodiment, the present invention relates to oral care compositions and methods as described above wherein the composition further comprises a TRPA1 enhancer selected from delta-damascone, cis-3-hexenyl cis-3-hexenoate, benzaldehyde dimethyl acetal, carvyl acetate, methyl benzyl butyrate, trans-2-nonen-1-ol, beta-ionol, geraniol, anisyl butyrate, ethyl isoeugenol, alpha-ionone, phenethyl salicylate, 2-phenyl propyl tetrahydrofuran, dihydro-alpha-ionone, thymyl methyl ether, cis-3-hexenyl hexanoate, 2,6,6-trimethyl-1-cyclohexene-1-acetaldehyde, ethyl salicylate, propyl 2,4-decadienoate, carvyl propionate, dihydroeugenol, and combinations thereof.

In another embodiment, the present invention relates to oral care compositions and methods as described above wherein the composition comprises from about 0.01% to about 0.1%, by weight of the composition, of the TRPA1 agonist which is selected from vanillin isobutyrate.

DETAILED DESCRIPTION OF THE INVENTION

The present invention relates to oral care compositions and use thereof, wherein such compositions have improved taste. Such compositions include a carrier material; from about 0.001 to about 10%, by weight of the composition, of an oral care component selected from metal salts, antimicrobial agents, bad breath reduction agents, bleaching agents, surfactants, or a combination thereof; and from about 0.001 to about 1%, by weight of the composition, of a TRPA1 agonist selected from vanillin esters; benzoate esters; hydroxybenzoate derivatives; methoxy benzoate derivatives; hydroxybutanedioate derivatives; benzamidobenzoate derivatives; methylpropanoate derivatives; phenyl acetate derivatives; hex-3-enoate derivatives; 2-(furan-2-ylmethylsulfanyl)-3-methylpyrazine; phenylmethoxymethylbenzene; (2R)-2-azaniumyl-3-[(2R)-2-azaniumyl-3-oxido-3-oxopropyl]disulfanylpropanoate; (3E)-2-hydroxy-4,8-dimethylnona-3,7-dienal; (2R)-2-azaniumyl-3-[(2S)-2-azaniumyl-3-oxido-3-oxopropyl]disulfanylpropanoate; (3Z)-3-butylidene-2-benzofuran-1-one; 3-methyl-N-(3-methylbutyl)butan-1-imine; 2-(furan-2-ylmethyldisulfanylmethyl)furan; and combinations thereof.

The present invention also relates to methods for improving taste of an oral care composition by adding such TRPA1 agonists to an oral care composition.

The term "dentifrice", as used herein, includes paste, gel, or liquid formulations unless otherwise specified. The dentifrice can be in a dual phase form, like a striped paste for example, and can also be used as a regimen.

The term "teeth", as used herein, refers to natural teeth as well as artificial teeth or dental prosthesis and is construed to include one tooth or multiple teeth.

The term "TRPA1" as used herein refers to the transient receptor potential cation channel, subfamily A, member 1, having a large cysteine-rich N-terminus that contains 18 predicted ankyrin repeats.

The term "TRPA1 activator" as used herein refers to any component which at a concentration of 1 mM gives a calcium flux count of at least 1000 counts above the background level of calcium present in the cell according to the FLIPR method as discussed herein. The term "count" is defined as the change in fluorescence of the transfected cell lines due to the influx of calcium across the cell membrane, which reacts with the calcium sensitive dye present within the cells.

The term "TRPA1 enhancer" as used herein refers to any component that boosts the calcium flux activity of a compound that directly activates TRPA1, but does not directly activate TRPA1.

As used herein, "oral care composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition may be in various forms including toothpaste, dentifrice, tooth gel, subgingival gel, mouthrinse, mousse, foam, mouthspray, lozenge, chewable tablet, chewing gum or denture product. In one embodiment, the oral care composition is in a form selected from toothpaste, dentifrice, tooth gel, mouth rinse or denture product. The oral care composition may also be incorporated onto strips or films for direct application or attachment to oral surfaces.

Active and other ingredients useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

These elements will be discussed in more detail below.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

Active and other ingredients useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

All measurements referred to herein are made at 25° C. (i.e. room temperature) unless otherwise specified.

As used herein, the word "about" means+/−10 percent.

As used herein, the word "include," and its variants, are intended to be non-limiting, such that recitation of items in a list is not to the exclusion of other like items that may also be useful in the materials, compositions, devices, and methods of this invention.

Oral Care Composition

Oral care compositions are often made up of a combination of components which can include carrier materials, surfactants, flavors, colorants, sensates, actives, and other additives. Other applicable oral care compositions would be personal health care products (such as cough syrups, cough drops and the like), pharmaceuticals, confectionaries, and foods, (such as chewing gum, soda and the like).

Carrier Material

The oral compositions of the present invention include from about 5% to about 80%, by weight of the composition, of a carrier material. In one embodiment, the compositions contain from about 10% to about 40%, by weight of the composition, of a carrier material.

Examples of materials which can act as a carrier material include water, glycerin, sorbitol, polyethylene glycols having a molecular weight of less than about 50,000, propylene glycol and other edible polyhydric alcohols, ethanol, or combinations thereof.

Oral Care Component

The oral compositions of the present invention comprise from about 0.0001% to about 8%, by weight of the composition. of at least one oral care component selected from metal salts, antimicrobial agents, bad breath reduction agents, bleaching agents, surfactants or a combination thereof. In one embodiment, the oral care composition comprises from about 0.01% to about 7%, alternatively from about 0.1% to about 5%, by weight of the composition, of the oral care component.

The compositions may further include a additional oral care component, discussed below as "optional oral care components". Such oral care actives are generally present in an amount of about 0.0001% to about 8%, by weight of the composition.

Metal Salts

The compositions of the present invention may contain from about 0.05% to about 11%, by weight of the oral care composition, of an oral care component selected from metal salts and combinations thereof. In other embodiments, the compositions contain from about 0.5% to about 7%, alternatively from about 1% to about 5%, by weight of the composition, of the metal salt.

Metal salts have a wide range of functions from antimicrobial agents to sensitivity agents and/or buffers. In one embodiment, the metal salt comprises a zinc salt, stannous salt, potassium salt, copper salt, or a combination thereof.

In one embodiment, the zinc salt is selected from zinc fluoride, zinc chloride, zinc iodide, zinc chlorofluoride, zinc actetate, zinc hexafluorozirconate, zinc sulfate, zinc lactate, zinc tartrate, zinc gluconate, zinc citrate, zinc malate, zinc glycinate, zinc pyrophosphate, zinc metaphosphate, zinc oxalate, zinc phosphate, zinc carbonate, and combinations thereof. In another embodiment, the zinc salt is selected from zinc chloride, zinc citrate, zinc gluconate, zinc lactate, zinc oxide, and combinations thereof.

In one embodiment, the potassium salt is selected from potassium nitrate, potassium citrate, potassium oxalate, potassium bicarbonate, potassium acetate, potassium chloride, and combinations thereof.

In one embodiment, the copper salt is selected from copper fluoride, copper chloride, copper iodide, copper chlorofluoride, copper actetate, copper hexafluorozirconate, copper sulfate, copper lactate, copper tartrate, copper gluconate, copper citrate, copper malate, copper glycinate, copper pyrophosphate, copper metaphosphate, copper oxalate, copper phosphate, copper carbonate, and combinations thereof. In a further embodiment, the copper salt is selected from copper gluconate, copper acetate, copper glycinate, and combinations thereof.

In another embodiment, the stannous salt is selected from stannous fluoride, stannous chloride, stannous iodide, stannous chlorofluoride, stannous actetate, stannous hexafluorozirconate, stannous sulfate, stannous lactate, stannous tartrate, stannous gluconate, stannous citrate, stannous malate, stannous glycinate, stannous pyrophosphate, stannous metaphosphate, stannous oxalate, stannous phosphate, stannous carbonate, and combinations thereof. In a further embodiment, the stannous salt is selected from stannous fluoride, stannous chloride, stannous chloride dihydrate, stannous fluoride, stannous lactate, stannous gluconate, stannous sulfate, and combinations thereof.

Dentifrices containing stannous salts, particularly stannous fluoride and stannous chloride, are described in U.S. Pat. No. 5,004,597 to Majeti et al. Other descriptions of stannous salts are found in U.S. Pat. No. 5,578,293 issued to Prencipe et al. and in U.S. Pat. No. 5,281,410 issued to Lukacovic et al. In addition to the stannous ion source, other ingredients needed to stabilize the stannous may be included, such as the ingredients described in Majeti et al. and Prencipe et al.

Some examples of metal salts which give an off taste include zinc chloride, zinc citrate, copper gluconate, zinc gluconate, or combinations thereof. The off taste associated with these types of metal salts are dirty, dry, earthy, metallic, sour, bitter, and astringent. See, for example, an article by Hu, Hongzhen, et al in *Nature Chemical Biology* (2009), 5 (3), Pages 183-190, entitled: *Zinc Activates Damage-Sensing TRPA1 Ion Channels.*

In one embodiment, the oral care composition contains from about 0.1 to about 7%, alternatively from about 1% to about 5%, alternatively from about 1.5% to about 3%, by weight of the oral care composition, of a metal salt selected from stannous salts and combinations thereof. In one embodiment, the oral care composition contains from about 0.01 to about 5%, alternatively from about 0.05% to about 4%, alternatively from about 0.1% to about 3.0%, by weight of the oral care composition, of a metal salt selected from zinc salts, copper salts, and combinations thereof.

Antimicrobial Agents

The compositions of the present invention may contain from about 0.035% or more, alternatively from about 0.1% to about 1.5%, alternatively from about 0.045% to about 1.0%, alternatively from about 0.05% to about 0.10%, by weight of the oral care composition, of an oral care component selected from antimicrobial agents.

One example of an antimicrobial agent useful herein is a quaternary ammonium compound. Those useful herein include, for example, those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethoylstearyl ammonium chloride, cetylpyridinium chloride, quaternized 5-amino-1, 3-bis(2-ethyl-hexyl)-5-methyl hexahydropyrimidine, benzalkonium chloride, benzethonium chloride and methyl benzethonium chloride are exemplary of typical quaternary ammonium antibacterial agents.

Other compounds include bis[4-(R-amino)-1-pyridinium] alkanes as disclosed in U.S. Pat. No. 4,206,215, Jun. 3, 1980, to Bailey. Other quaternary ammonium compounds include the pyridinium compounds. Examples of pyridinium quaternary ammonium compounds include cetylpyridinium and tetradecylpyridinium halide salts (i.e., chloride, bromide, fluoride and iodide).

The oral care compositions of the present invention may also include other antimicrobial agents including non-cationic antimicrobial agents such as halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilides. Also useful antimicrobials are enzymes, including endoglycosidase, papain, dextranase, mutanase, and combinations thereof. Such agents are disclosed in U.S. Pat. No. 2,946,725, Jul. 26, 1960, to Norris et al. and in U.S. Pat. No. 4,051,234 to Gieske et al. Examples of other antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, and U.S. Pat. No. 4,894,220 to Nabi et al.

Of the above antimicrobial agents, examples of some which provide an unwanted taste include, for example, chlorhexidine, triclosan, and thymol. The unwanted tastes often associated with these types of antimicrobial agents include bitter, dirty, earthy, sour, and/or astringent.

Bad Breath Reduction Agents

The compositions of the present invention may contain from about 0.01% to about 4.0%, by weight of the composition, of an oral care component selected from bad breath reduction agents. These agents generally work to reduce breath malodor.

Examples of bad breath reduction agents include copper salts and carbonyl compounds such as ascorbic acid [3-oxo-L-gulofuranolactone]; cis-jasmone [3-methyl-2-(2-pentenyl-2-cyclopentenone]; 2,5-dimethyl-4-hydroxy-3(2H)-furanone; 5-ethyl-3-hydroxy-4-methyl-2(5H)-furanone; vanillin [4-hydroxy-3-methoxybenzaldehyde]; ethyl vanillin; anisaldehyde [4-methoxybenzaldehyde]; 3,4-methylenedioxybenzaldehyde; 3,4-dimethoxybenzaldehyde; 4-hydroxybenzaldehyde; 2-methoxybenzaldehyde; benzaldehyde; cinnamaldehyde [3-phenyl-2-propenal]; hexyl cinnamaldehyde; α-methyl cinnamaldehyde; ortho-methoxy cinnamaldehyde; citral; linalool; geraniol; eugenol; or combinations thereof. Without being limited by theory, it is believed some bad breath reduction agents work as "traps" by reacting with the thiol or sulfide and forming products with less odor impact. Of these bad breath reduction agents, an example of one which provide an unwanted taste within an oral care composition include, for example, anisaldehyde.

The unwanted tastes often associated with these types of bad breath reduction agents include chemical, plastic, bitter, and/or sour.

Bleaching Agents

The compositions of the present invention may contain from about 0.01% to about 30%, alternatively from about 0.1% to about 10%, alternatively from about 0.5% to about 5%, by weight of the composition, of an oral care component selected from bleaching agents. Bleaching agents are generally agents which whiten teeth.

Examples of bleaching agents include peroxides, perborates, percarbonates, peroxyacids, persulfates, and combinations thereof. Suitable peroxide compounds include hydrogen peroxide, urea peroxide, calcium peroxide, sodium peroxide, zinc peroxide, or combinations thereof. One example of a percarbonate is sodium percarbonate. An example of a persulfate includes oxones. The following amounts represent the amount of peroxide raw material, although the peroxide source may contain ingredients other than the peroxide raw material. For example, the peroxide source could be a solution a peroxide raw material and a carrier material. Of these bleaching agents, examples of some which provide an unwanted taste within an oral care composition include, for example, peroxide and percarbonate. The unwanted tastes often associated with these bleaching agents include dirty, chemical, and/or sour.

Surfactants

The compositions of the present invention may contain from about 0.1% to about 15%, alternatively from about 0.5% to about 5%, by weight of the composition, of an oral care component selected from surfactants. The surfactant may be selected from anionic, nonionic, amphoteric, zwitterionic, cationic, or combinations thereof.

Anionic surfactants useful herein include, for example, the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Other suitable anionic surfactants include sarcosinates, such as sodium lauroyl sarcosinate, taurates, sodium lauryl sulfoacetate, sodium lauroyl isethionate, sodium laureth carboxylate, and sodium dodecyl benzenesulfonate. Combinations of anionic surfactants can also be employed. Many suitable anionic surfactants are disclosed by Agricola et al., U.S. Pat. No. 3,959,458. In varying embodiments, the present compositions comprise an anionic surfactant at a level of from about 0.025% to about 9%, from about 0.05% to about 5%, or from about 0.1% to about 1%.

Another class of anionic surfactants useful here are alkyl phosphates. The surface active organophosphate agents have a strong affinity for enamel surface and have sufficient surface binding propensity to desorb pellicle proteins and remain affixed to enamel surfaces. Suitable examples of organophosphate compounds include mono-, di- or triesters represented by the general structure below wherein Z1, Z2, or Z3 may be identical or different, at least one being an organic moiety, in one embodiment selected from linear or branched, alkyl or alkenyl group of from 1 to 22 carbon atoms, optionally substituted by one or more phosphate groups; alkoxylated alkyl or alkenyl, (poly)saccharide, polyol or polyether group.

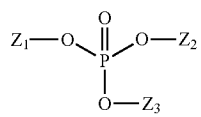

Some other agents include alkyl or alkenyl phosphate esters represented by the following structure:

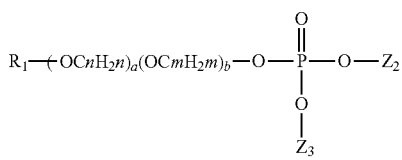

wherein R1 represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; Z2 and Z3 may be identical or different, each represents hydrogen, alkali metal, ammonium, protonated alkyl amine or protonated functional alkyl amine such as an alkanolamine, or a R1-(OCnH2n)a(OCmH2m)b- group. Examples of suitable agents include alkyl and alkyl (poly)alkoxy phosphates such as lauryl phosphate; PPG5 ceteareth-10 phosphate; Laureth-1 phosphate; Laureth-3 phosphate; Laureth-9 phosphate; Trilaureth-4 phosphate; C12-18 PEG 9 phosphate; Sodium dilaureth-10 phosphate. In one embodiment, the alkyl phosphate is polymeric. Examples of polymeric alkyl phosphates include those containing repeating alkoxy groups as the polymeric portion, in particular 3 or more ethoxy, propoxy isopropoxy or butoxy groups.

Additional suitable polymeric organophosphate agents include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol) phosphate, PEG cyclodextrin phosphate, PEG sorbitan phosphate, PEG alkyl sorbitan phosphate, and PEG methyl glucoside phosphate. Suitable non-polymeric phosphates include alkyl mono glyceride phosphate, alkyl sorbitan phosphate, alkyl methyl glucoside phosphate, alkyl sucrose phosphates.

Another suitable surfactant is one selected from sarcosinate surfactants, isethionate surfactants and taurate surfactants. In one embodiment, an alkali metal or ammonium salts of these surfactants are used. Examples of those sodium and potassium salts include following: lauroyl sarcosinate, myristoyl sarcosinate, palmitoyl sarcosinate, stearoyl sarcosinate and oleoyl sarcosinate, or combinations thereof. Of these anionic surfactants, examples of some which provide an unwanted taste within an oral care composition include, for example, SLS, lauroyl sarcosinate, and/or fatty alcohols or acids associated with natural based surfactants. The unwanted tastes often associated with these surfactants are soapy, chemical, and/or artificial.

Zwitterionic or amphoteric surfactants useful in oral care compositions include derivatives of aliphatic quaternary ammonium, phosphonium, and sulfonium compounds, in which the aliphatic radicals can be straight chain or branched, and one of the aliphatic substituents contains from about 8 to 18 carbon atoms and one contains an anionic water-solubilizing group, e.g., carboxy, sulfonate, sulfate, phosphate or phosphonate. Suitable betaine surfactants are disclosed in U.S. Pat. No. 5,180,577 to Polefka et al. Typical alkyl dimethyl betaines include decyl betaine or 2-(N-decyl-N,N-dimethylammonio) acetate, coco betaine or 2-(N-Coco-N,N-dimethyl ammonio) acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine (CADB), and lauramidopropyl betaine. Of these surfactants, examples of some which provide an unwanted taste within an oral care composition include, for example, cocoamidopropyl betaine and lauryl betaine. The unwanted tastes often associated with these types of surfactants are soapy and chemical. These surfactants are generally included in an oral care composition in a range of about 0.5% to about 5%.

Cationic surfactants useful in the present invention include, for example, derivatives of quaternary ammonium compounds having one long alkyl chain containing from about 8 to 18 carbon atoms such as lauryl trimethylammonium chloride; cetyl pyridinium chloride; cetyl trimethylammonium bromide; coconut alkyltrimethylammonium nitrite; cetyl pyridinium fluoride or combinations thereof. Additional quaternary ammonium fluorides having detergent properties are described in U.S. Pat. No. 3,535,421 to Briner et al. Of these surfactants, examples of some which provide an unwanted taste within an oral care composition include, for example, cetyl pyridinium chloride or chlorhexidine. The unwanted tastes often associated with these surfactants are chemical and/or antiseptic.

Nonionic surfactants that can be used in the compositions of the present invention include, for example, compounds produced by the condensation of alkylene oxide groups (hydrophilic in nature) with an organic hydrophobic compound which may be aliphatic or alkylaromatic in nature. Examples of suitable nonionic surfactants include the Pluronics® which are poloxamers, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and combinations of such materials.

TRPA1 Agonist

The oral compositions of the present invention comprise from about 0.0001% to about 1%, alternatively from about 0.0001% to about 0.4%, still alternatively from about 0.001% to about 0.3%, by weight of the composition, of a TRPA1 agonist selected from vanillin esters and structurally similar compounds. Without being limited by theory, vanillin esters, although suitable off-taste mitigators, may not be structurally suitable for all formulations. In oral care compositions having a relatively low pH (<6.0) or high pH (>8.0), ester hydrolysis may occur. Some of the linear derivatives, where they have unprotected esters, may undergo hydrolysis. Therefore, one of the structural derivatives would be chosen to suit the formula environment.

Examples of vanillin esters and structurally similar compounds useful herein include: vanillin esters; benzoate esters; hydroxybenzoate derivative; methoxy benzoate derivatives; hydroxybutanedioate derivatives; benzamidobenzoate derivatives; methylpropanoate derivatives; phenyl acetate derivatives; hex-3-enoate derivatives; 2-(furan-2-ylmethylsulfanyl)-3-methylpyrazine; phenylmethoxymethylbenzene; (2R)-2-azaniumyl-3-[(2R)-2-azaniumyl-3- oxido-3-oxopropyl]disulfanylpropanoate; (3E)-2-hydroxy-4,8-dimethylnona-3,7-dienal; (2R)-2-azaniumyl-3-[(2R)-2-azaniumyl-3-oxido-3-oxopropyl]disulfanylpropanoate; (3Z)-3-butylidene-2-benzofuran-1-one; 3-methyl-N-(3-methylbutyl)butan-1-imine; 2-(furan-2-ylmethyldisulfanylmethyl)furan, and combinations thereof.

Vanillin Esters

In one embodiment, the composition comprises from about 0.0001% to about 1%, alternatively from about 0.0001% to about 0.4%, by weight of the composition, of the TRPA1 agonist which is selected from vanillin esters. Without being limited by theory, such levels are lower than that typically utilized to impart a sweet flavor but are high enough to act as the TRPA1 agonist. One benefit to using lower levels of vanillin esters is that the molecule will not interfere with the character of an added flavor, such as peppermint or spearmint.

Vanillin esters are identified as esterified vanillin according to the structure below:

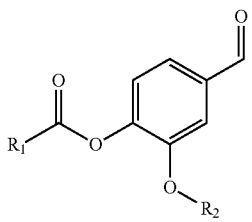

Where R1=linear or branched or cyclic, C1 to C22 alkyl, alkene, alkyne. R2=hydrogen, linear or branched, C1 to C6 alkyl, alkene, alkyne. The preferred esters are C1-C6 linear or branched alkyl or alkene chains. The most preferred are acetate, formate, propionate, and butyrate esters.

Examples of vanillin esters include: vanillin isobutyrate, ethyl vanillin isobutyrate, vanillin acetate, vanillin formate, vanillin propionate, vanillin butyrate, vanillin valerate, vanillin caproate, vanillin myrisate, vanillin laurate, vanillin palmitate, vanillin oleate, vanillin stearate, and combinations thereof. In one embodiment, the vanillin ester is selected from vanillin acetate, vanillin formate, vanillin propionate, vanillin butyrate, and combinations thereof. In one embodiment, the composition comprises from about 0.001% to about 0.085%, alternatively from about 0.002% to about 0.007%, by weight of the composition of the TRPA1 agonist selected from vanillin isobutyrate. In one embodiment, the vanillin ester is vanillin propionate.

Structurally Similar Compounds

In one embodiment, the composition comprises from about 0.0001% to about 1%, alternatively from about 0.0001% to about 0.4%, by weight of the composition, of the TRPA1 agonist which is selected from compounds structurally similar to vanillin esters. Such compounds may be identified using one of two methods; Daylight fingerprint based similarity searching; and molecular shape based similarity searching. Both algorithms are implemented in the Chemistry Development Kit (CDK), an open-source java library.

In fingerprint based similarity search, vanillin isobutyrate and each candidate compound is represented by a fingerprint or a bit string (a sequence of 0 and 1 digit), which is derived from enumeration of all linear substructures of length N in each compound. The similarity of one compound to vanillin isobutyrate is calculated using Tanimoto coefficient, T, which is defined as $T=c/(a+b+c)$, where c is the count of the bits on (digit 1) in both compounds; a is the count of bits on in vanillin isobutyrate but not in the candidate compound; b is the count of bits on in candidate compound but not in vanillin isobutyrate.

In molecular shape based similarity search, first the distributions of atomic distances to 4 specific points for vanillin isobutyrate and candidate compounds is calculated: the centroid of the compound, the atom that is closest to the centroid, the atom that is farthest from the centroid and the atom that is farthest from the previous point. This will generate 4 sets of distance distributions. Each compound is then represented by a vector of 12 shape descriptors derived from the first three moments of each distance distribution. The similarity between vanillin isobutyrate and a candidate compound is evaluated using the inverse of a normalized Manhattan type metric.

Structurally similar compounds useful herein include those shown below in Table I:

TABLE I

Structurally Similar Compounds

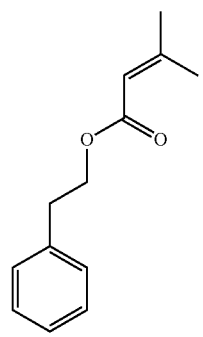

IUPAC: phenethyl 3-methylbut-2-enoate
Molecular Formula: C13H16O2
Molecular Weight: 204.26494
XLogP3: null
TPSA: 26.3
H-Bond Donor: 0
H-Bond Acceptor: 2
CAS: 42078-65-9
FEMA: 2869

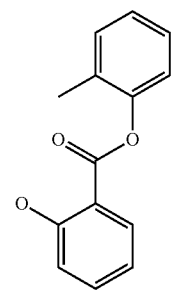 [SMILES: Cc1ccccc1OC(=O)c1ccccc1O]

IUPAC: (2-methylphenyl) 2-hydroxybenzoate
Molecular Formula: C14H12O3
Molecular Weight: 228.24328
XLogP3: null
TPSA: 46.5
H-Bond Donor: 1
H-Bond Acceptor: 3
CAS: 617-01-6
FEMA: 3734

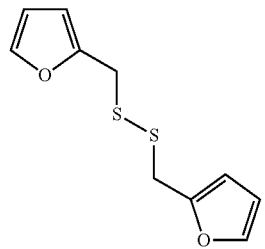 [SMILES: c1coc(CSSCc2ccco2)c1]

IUPAC: 2-(furan-2-ylmethyldisulfanyl-methyl)furan
Molecular Formula: C10H10O2S2
Molecular Weight: 226.3152
XLogP3: 2.1
TPSA: 26.3
H-Bond Donor: 0
H-Bond Acceptor: 2
CAS: 4437-20-1
FEMA: 3146

TABLE I-continued

Structurally Similar Compounds

| Structure | Details |
|---|---|
| (isobutyl-N=CH-CH2-isobutyl imine) | IUPAC: 3-methyl-N-(3-methylbutyl)butan-1-imine<br>Molecular Formula: C10H21N<br>Molecular Weight: 155.28044<br>XLogP3: 2.8<br>TPSA: 12.4<br>H-Bond Donor: 0<br>H-Bond Acceptor: 1<br>CAS: 35448-31-8<br>FEMA: 3990 |
| (3Z)-3-butylidene-benzofuranone structure | IUPAC: (3Z)-3-butylidene-2-benzofuran-1-one<br>Molecular Formula: C12H12O2<br>Molecular Weight: 188.22248<br>XLogP3: 3.2<br>TPSA: 26.3<br>H-Bond Donor: 0<br>H-Bond Acceptor: 2<br>CAS: 551-08-6<br>FEMA: 3333<br>Natural CAS: 551-08-6 |
| isobutyl salicylate structure | IUPAC: 2-methylpropyl 2-hydroxybenzoate<br>Molecular Formula: C11H14O3<br>Molecular Weight: 194.22706<br>XLogP3: null<br>TPSA: 46.5<br>H-Bond Donor: 1<br>H-Bond Acceptor: 3<br>CAS: 87-19-4<br>FEMA: 2213<br>Natural CAS: 87-19-4 |
| cystine structure | IUPAC: (2R)-2-azaniumyl-3-[(2S)-2-azaniumyl-3-oxido-3-oxopropyl]disulfanylpropanoate<br>Molecular Formula: C6H12N2O4S2<br>Molecular Weight: 240.30048<br>XLogP3: −5<br>TPSA: 136<br>H-Bond Donor: 2<br>H-Bond Acceptor: 4<br>CAS: 923-32-0 |
| (3E)-2-hydroxy-4,8-dimethylnona-3,7-dienal structure | IUPAC: (3E)-2-hydroxy-4,8-dimethylnona-3,7-dienal<br>Molecular Formula: C11H18O2<br>Molecular Weight: 182.25942<br>XLogP3: 2.6<br>TPSA: 37.3<br>H-Bond Donor 1<br>H-Bond Acceptor: 2<br>CAS: 2142-94-1<br>FEMA: 2776 |
| cis-3-hexenyl anthranilate structure | IUPAC: [(Z)-hex-3-enyl] 2-aminobenzoate<br>Molecular Formula: C13H17NO2<br>Molecular Weight: 219.27958<br>XLogP3: null<br>TPSA: 52.3<br>H-Bond Donor: 1<br>H-Bond Acceptor: 3<br>CAS: 65405-76-7<br>FEMA: 3925 |
| 2-(3-methylbutoxy)ethylbenzene structure | IUPAC: 2-(3-methylbutoxy)ethylbenzene<br>Molecular Formula: C13H20O<br>Molecular Weight: 192.2973<br>XLogP3: 3.7<br>TPSA: 9.2<br>H-Bond Donor: 0<br>H-Bond Acceptor: 1<br>CAS: 54173-86-3, 56011-02-0<br>FEMA: 4635 |
| ethyl 4-methoxybenzoate structure | IUPAC: ethyl 4-methoxybenzoate<br>Molecular Formula: C10H12O3<br>Molecular Weight: 180.20048<br>XLogP3: null<br>TPSA: 35.5<br>H-Bond Donor: 0<br>H-Bond Acceptor: 3<br>CAS: 94-30-4<br>FEMA: 2420 |
| difurfuryl ether structure | IUPAC: 2-(furan-2-ylmethoxymethyl)furan<br>Molecular Formula: C10H10O3<br>Molecular Weight: 178.1846<br>XLogP3: 1.3<br>TPSA: 35.5<br>H-Bond Donor: 0<br>H-Bond Acceptor 3<br>CAS: 4437-22-3<br>FEMA: 3337 |

TABLE I-continued

Structurally Similar Compounds

IUPAC: diethyl (2S)-2-hydroxybutanedioate
Molecular Formula: C8H14O5
Molecular Weight: 190.19376
XLogP3: 0.1
TPSA: 72.8
H-Bond Donor: 1
H-Bond Acceptor: 5
CAS: 626-11-9, 691-84-9
FEMA: 2374
Natural CAS: 691-84-9

IUPAC: diethyl 2-hydroxybutanedioate
Molecular Formula: C8H14O5
Molecular Weight: 190.19376
XLogP3: 0.1
TPSA: 72.8
H-Bond Donor: 1
H-Bond Acceptor: 5
CAS: 121401-63-6, 626-11-9, 7554-12-3
FEMA: 2374

IUPAC: phenyl butanoate
Molecular Formula: C10H12O2
Molecular Weight: 164.20108
XLogP3: null
TPSA: 26.3
H-Bond Donor: 0
H-Bond Acceptor: 2
CAS: 4346-18-3
FEMA: 4621

IUPAC: propyl benzoate
Molecular Formula: C10H12O2
Molecular Weight: 164.20108
XLogP3: null
TPSA: 26.3
H-Bond Donor: 0
H-Bond Acceptor: 2
CAS: 2315-68-6
FEMA: 2931

IUPAC: phenyl 2-hydroxybenzoate
Molecular Formula: C13H10O3
Molecular Weight: 214.2167
XLogP3: null
TPSA: 46.5
H-Bond Donor: 1
H-Bond Acceptor: 3
CAS: 118-55-8
FEMA: 3960
Natural CAS: 118-55-8

IUPAC: propan-2-yl 2-phenylacetate
Molecular Formula: C11H14O2
Molecular Weight: 178.22766
XLogP3: null
TPSA: 26.3
H-Bond Donor: 0
H-Bond Acceptor: 2
CAS: 4861-85-2
FEMA: 2956

IUPAC: (2R)-2-azaniumyl-3-[(2R)-2-azaniumyl-3-oxido-3-oxopropyl]disulfanylpropanoate
Molecular Formula: C6H12N2O4S2
Molecular Weight: 240.30048
XLogP3: −5
TPSA: 136
H-Bond Donor: 2
H-Bond Acceptor: 4
CAS: 56-89-3
Natural CAS: 56-89-3

IUPAC: 2-(furan-2-ylmethylsulfanyl)-3-methylpyrazine
Molecular Formula: C10H10N2OS
Molecular Weight: 206.2642
XLogP3: 1.6
TPSA: 38.9
H-Bond Donor: 0
H-Bond Acceptor: 3
CAS: 102129-35-1, 59035-98-2, 59303-07-0
FEMA: 2371

IUPAC: phenylmethoxy-methylbenzene
Molecular Formula: C14H14O
Molecular Weight: 198.26036
XLogP3: null
TPSA: 9.2
H-Bond Donor: 0
H-Bond Acceptor: 1
CAS: 103-50-4
FEMA: 2371

IUPAC: 2-benzamidobenzoate
Molecular Formula: C14H10NO3—
Molecular Weight: 240.2341
XLogP3: null
TPSA: 69.2
H-Bond Donor: 1
H-Bond Acceptor: 3
CAS: 579-93-1
FEMA: 4078
Natural CAS: 579-93-1

TABLE I-continued

Structurally Similar Compounds

| Structure | Details |
|---|---|
| | IUPAC: [(Z)-hex-3-enyl] (Z)-hex-3-enoate<br>Molecular Formula: C12H20O2<br>Molecular Weight: 196.286<br>XLogP3: 3.3<br>TPSA: 26.3<br>H-Bond Donor: 0<br>H-Bond Acceptor: 2<br>CAS: 61444-38-0<br>FEMA: 3689 |
| | IUPAC: (4-formyl-2-methoxyphenyl) acetate<br>Molecular Formula: C10H10O4<br>Molecular Weight: 194.184<br>XLogP3: null<br>TPSA: 52.6<br>H-Bond Donor: 0<br>H-Bond Acceptor: 4<br>CAS: 881-68-5, 4736-37-2<br>FEMA: 3108<br>Natural CAS: 881-68-5 |
| | IUPAC: (2-methoxyphenyl) propanoate<br>Molecular Formula: C10H12O3<br>Molecular Weight: 180.20048<br>XLogP3: null<br>TPSA: 35.5<br>H-Bond Donor: 0<br>H-Bond Acceptor: 3<br>CAS: 7598-60-9<br>FEMA: 4609 |
| | IUPAC: (2-methoxy-4-prop-2-enylphenyl) 3-methylbutanoate<br>Molecular Formula: C15H20O3<br>Molecular Weight: 248.3175<br>XLogP3: null<br>TPSA: 35.5<br>H-Bond Donor: 0<br>H-Bond Acceptor: 3<br>CAS: 61114-24-7<br>FEMA: 4118<br>Natural CAS: 61114-24-7 |
| | IUPAC: (4-methylphenyl) 2-methylpropanoate<br>Molecular Formula: C11H14O2<br>Molecular Weight: 178.22766<br>XLogP3: null<br>TPSA: 26.3<br>H-Bond Donor: 0<br>H-Bond Acceptor: 2<br>CAS: 103-93-5<br>FEMA: 3075 |
| | IUPAC: 3-ethoxy-4-hydroxybenzaldehyde<br>Molecular Formula: C9H10O3<br>Molecular Weight: 166.1739<br>XLogP3: null<br>TPSA: 46.5<br>H-Bond Donor: 1<br>H-Bond Acceptor: 3<br>CAS: 121-32-4<br>FEMA: 2464<br>Natural CAS: 121-32-4 |
| | IUPAC: [2-methoxy-4-[(E)-prop-1-enyl]phenyl] acetate<br>Molecular Formula: C12H14O3<br>Molecular Weight: 206.23776<br>XLogP3: null<br>TPSA: 35.5<br>H-Bond Donor: 0<br>H-Bond Acceptor: 3<br>CAS: 93-29-8<br>FEMA: 2470 |

TRPA1 Enhancer

The compositions of the present invention may further comprise from about 0.001% to about 3.0%, alternatively from about 0.005% to about 1.0%, by weight of the composition, of a TRPA1 enhancer selected from delta-damascone, cis-3-hexenyl cis-3-hexenoate, benzaldehyde dimethyl acetal, carvyl acetate, methyl benzyl butyrate, trans-2-nonen-1-ol, beta-ionol, geraniol, anisyl butyrate, ethyl isoeugenol, alpha-ionone, phenethyl salicylate, 2-phenyl propyl tetrahydrofuran, dihydro-alpha-ionone, thymyl methyl ether, cis-3-hexenyl hexanoate, 2,6,6-trimethyl-1-cyclohexene-1-acetaldehyde, ethyl salicylate, propyl 2,4-decadienoate, carvyl propionate, dihydroeugenol, and combinations thereof.

Optional Oral Care Components

The compositions of the present invention may also contain from about 0.0001% to about 8%, alternatively from about 0.001% to about 5%, by weight of the composition, of an optional oral care component. Optional oral care components include flavors, anti-tartar agents, colorants, sensates, sweeteners, abrasive polishing materials, anticaries agents, and combinations thereof.

Flavors

Another component which can be part of an oral care composition includes flavors. Flavors are generally present in an amount of about 0.4% to about 3% by weight of the oral care composition. Examples of some flavors and flavor components used in oral care compositions are mint oils, wintergreen, clove bud oil, cassia, sage, parsley oil, marjoram, lemon, orange, propenyl guaethol, heliotropine, 4-cis-heptenal, diacetyl, methyl-p-tert-butyl phenyl acetate, methyl salicylate, ethyl salicylate, 1-menthyl acetate, oxanone, α-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, α-terpineol, linalool, limonene, citral, neral, geranial, geraniol nerol, maltol, ethyl maltol, anethole, dihydroanethole, carvone, menthone, β-damascenone, ionone, γ-decalactone, γ-nonalactone, γ-undecalactone, or combinations thereof. Generally suitable flavoring ingredients are chemicals with structural features and functional groups that are less prone to redox reactions. These include derivatives of flavor chemicals that are saturated or contain stable aromatic rings or ester groups. Of these flavors, examples of some which provide an unwanted taste include, for example, citral, geranial, eucalyptol, and eugenol. The unwanted tastes often associated with these types of flavors are sourness, chemical, bitter, pungent, and/or astringent.

Anti-Tartar Agents

Another component which can be part of an oral care composition includes anti-tartar agents. One example of an antitartar agent is a pyrophosphate salt as a source of pyrophosphate ion. The pyrophosphate salts useful in the present compositions include, for example, the mono-, di- and tetraalkali metal pyrophosphate salts and combinations thereof. Disodium dihydrogen pyrophosphate (Na2H2P2O7), sodium acid pyrophosphate, tetrasodium pyrophosphate (Na4P2O7), and tetrapotassium pyrophosphate (K4P2O7) in their unhydrated as well as hydrated forms are further species. In compositions of the present invention, the pyrophosphate salt may be present in one of three ways: predominately dissolved, predominately undissolved, or a combination of dissolved and undissolved pyrophosphate. The amount of pyrophosphate salt useful in making these compositions is any tartar control effective amount. In varying embodiments, the amount of pyrophosphate salt is from about 1.5% to about 15%, from about 2% to about 10%, or about 3% to about 8%, by weight of the oral care composition.

Colorants

Another component which can be part of an oral care composition includes colorants.

Colorants are generally present in an amount of about 0.001% to about 0.5%, by weight of the oral care composition. Examples of some colorants used in oral care compositions include D&C Yellow No. 10, FD&C Blue No. 1, FD&C Red No. 40, D&C Red No. 33 and combinations thereof. In one embodiment, the composition comprises from about 0.0001% to about 0.1%, alternatively from about 0.001% to about 0.01%, by weight of the oral care composition, of a colorant. Of these colorants, an example of a colorant which provides an unwanted taste includes, for example, D&C Red No. 33. The unwanted tastes often associated with this colorant are metallic, sharp, and/or chemical.

Sensates

Another component which can be part of an oral care composition is a sensate. Sensate molecules such as cooling, warming, and tingling agents are useful to deliver signals to the consumer. Sensates are generally present in an amount of from about 0.001% to about 0.8%, by weight of the oral care composition. The most well-known cooling sensate compound is menthol, particularly l-menthol, which is found naturally in peppermint oil. Other isomers of menthol (neomenthol, isomenthol and neoisomenthol) have somewhat similar, but not identical odor and taste, i.e., having disagreeable notes described as earthy, camphor, musty, etc. The biggest difference among the isomers is in their cooling potency. L-menthol provides the most potent cooling, i.e., having the lowest cooling threshold of about 800 ppb, i.e., the concentration level where the cooling effect could be clearly recognized. At this level, there is no cooling effect for the other isomers.

A large number of coolant compounds of natural or synthetic origin have been described. The most well-known compound is menthol, particularly l-menthol, which is found naturally in peppermint oil, notably of *Mentha arvensis* L and *Mentha viridis* L. Of the isomers of menthol, the l-isomer occurs most widely in nature and is typically what is referred by the name menthol having coolant properties. L-menthol has the characteristic peppermint odor, has a clean fresh taste and exerts a cooling sensation when applied to the skin and mucosal surfaces. Other isomers of menthol (neomenthol, isomenthol and neoisomenthol) have somewhat similar, but not identical odor and taste, i.e., some having disagreeable notes described as earthy, camphor, musty. The biggest difference among the isomers is in their cooling potency. L-menthol provides the most potent cooling, i.e., having the lowest cooling threshold of about 800 ppb, i.e., the concentration where the cooling effect could be clearly recognized. At this level, there is no cooling effect for the other isomers. For example, d-neomenthol is reported to have a cooling threshold of about 25,000 ppb and 1-neomenthol about 3,000 ppb. [R. Emberger and R. Hopp, "Synthesis and Sensory Characterization of Menthol Enantiomers and Their Derivatives for the Use in Nature Identical Peppermint Oils," Specialty Chemicals (1987), 7(3), 193-201]. This study demonstrated the outstanding sensory properties of l-menthol in terms or cooling and freshness and the influence of stereochemistry on the activity of these molecules.

Among synthetic coolants, many are derivatives of or are structurally related to menthol, i.e., containing the cyclohexane moiety, and derivatized with functional groups including carboxamide, ketal, ester, ether and alcohol. Examples include the ρ-menthanecarboxamide compounds such as N-ethyl-ρ-menthan-3-carboxamide, known commercially as "WS-3", and others in the series such as WS-5 (N-ethoxycarbonylmethyl-ρ-menthan-3-carboxamide), WS-12 [N-(4-methoxyphenyl)-ρ-menthan-3-carboxamide] and WS-14 (N-tert-butyl-ρ-menthan-3-carboxamide). Examples of menthane carboxy esters include WS-4 and WS-30. An example of a synthetic carboxamide coolant that is structurally unrelated to menthol is N,2,3-trimethyl-2-isopropylbutanamide, known as "WS-23". Additional examples of synthetic coolants include alcohol derivatives such as 3-(1-menthoxy)-propane-1,2-diol known as TK-10, isopulegol (under the tradename Coolact P) and ρ-menthane-3,8-diol (under the tradename Coolact 38D) all available from Takasago; menthone glycerol acetal known as MGA; menthyl esters such as menthyl acetate, menthyl acetoacetate, menthyl lactate known as Frescolat® supplied by Haarmann and Reimer, and monomenthyl succinate under the tradename Physcool from V. Mane. TK-10 is described in U.S. Pat. No. 4,459,425 to Amano et al. Other alcohol and ether derivatives of menthol are described e.g., in GB 1,315,626 and in U.S. Pat. Nos. 4,029,759; 5,608,119; and 6,956,139. WS-3 and other carboxamide cooling agents are described for example in U.S. Pat. Nos. 4,136,163; 4,150,052; 4,153,679; 4,157,384; 4,178,459 and 4,230,688. Additional N-substituted ρ-menthane carboxamides are described in WO 2005/049553A1 including N-(4-cyanomethylphenyl)-ρ-menthanecarboxamide, N-(4-sulfamoylphenyl)-ρ-menthanecarboxamide, N-(4-cyanophenyl)ρ-menthanecarboxamide, N-(4-acetylphenyl)-ρ-menthanecarboxamide, N-(4-hydroxymethylphenyl)-ρ-menthanecarboxamide and N-(3-hydroxy-4- methoxyphenyl)-ρ-menthanecarboxamide. Other N-substituted ρ-menthane carboxamides include amino acid derivatives such as those disclosed in WO 2006/103401 and in U.S. Pat. Nos. 4,136,163; 4,178,459 and 7,189,760 such as N-((5-methyl-2-(1-methylethyl)cyclohexyl)carbonyl)glycine ethyl ester and N-((5-methyl-2-(1-methylethyl)cyclohexyl)carbonyl)alanine ethyl ester. Menthyl esters including those of amino acids such as glycine and alanine are disclosed e.g., in EP 310,299 and in U.S. Pat. Nos. 3,111,127; 3,917,613; 3,991,178; 5,703,123; 5,725,865; 5,843,466; 6,365,215; 6,451,844; and 6,884,903. Ketal derivatives are described, e.g., in U.S. Pat. Nos. 5,266,592; 5,977,166 and 5,451,404. Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., J. Pharm. Pharmacol. (1983), 35:110-112. Reviews on the coolant activity of menthol and synthetic coolants include H. R. Watson, et al. J. Soc. Cosmet. Chem. (1978), 29, 185-200 and R. Eccles, J. Pharm. Pharmacol., (1994), 46, 618-630.

Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., J. Pharm. Pharmacol. (1983), 35:110-112. Of these cooling sensates, examples of some which provide an unwanted taste include, for example, menthol and menthone. The unwanted tastes often associated with these cooling sensates include burning, chemical, and/or medicinal.

Some examples of warming sensates include ethanol; capsicum; nicotinate esters, such as benzyl nicotinate; polyhydric alcohols; capsicum powder; a capsicum tincture; capsicum extract; capsaicin; homocapsaicin; homodihydrocapsaicin; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof. Warming sensates are generally included in an oral care composition at a level of about 0.05% to about 2%, by weight of the composition.

In one embodiment, compositions of the present invention comprise vanillyl butyl ether. In one embodiment, a composition comprises vanillin isobutyrate in an amount from about 0.0001% to about 0.02%, by weight of the composition, and vanillyl butyl ether in an amount from about 0.0001% to about 0.02%, by weight of the composition. In one embodiment, vanillin isobutyrate and vanillyl butyl ether are in the composition in an about 1:1 ratio.

Examples of some tingling sensates include, jambu Oleoresin, Zanthoxylum peperitum, saanshool-I, saanshool II, sanshoamide, piperine, piperidine, eugenol, spilanthol, 4-(1-methoxymethyl)-2-phenyl-1,3-dioxolane, or combinations thereof. Tingling sensates are generally included in an oral care composition at a level of about 0.0005% to about 1%, by weight of the composition. Of these tingling sensates, examples of some which provide an unwanted taste within an oral care composition include, for example, jambu, saanshool, and/or eugenol. The unwanted taste(s) often associated with these tingling sensates include a peppery, bitter, and/or metallic taste.

Sweeteners

Another component which can be part of an oral care composition includes sweeteners. Examples of sweeteners useful herein include those selected from saccharin, chlorosucrose (sucralose), steviolglycosides, rebaudioside A, rebaudioside B, rebaudioside C, rebaudioside D, rebaudioside E, rebaudioside F, dulcoside A, dulcoside B, rubusoside, stevia, stevioside, acesulfame K, xylitol, neohesperidine DC, alitame, aspartame, neotame, alitame, thaumatin, cyclamate, glycyrrhizin, mogroside IV, mogroside V, Luo Han Guo sweetener, siamenoside, monatin and its salts (monatin SS, RR, RS, SR), curculin, monellin, mabinlin, brazzein, hemandulcin, phyllodulcin, glycyphyllin, phloridzin, trilobtain, baiyanoside, osladin, polypodoside A, pterocaryoside A, pterocaryoside B, mukurozioside, phlomisoside I, periandrin I, abrusoside A, cyclocarioside I,N—[N-[3-(3-hydroxy-4-methoxyphenyl)propyl]-L-α-aspartyl]-L-phenylalanine 1-methyl ester, N—[N-[3-(3-hydroxy-4-methoxyphenyl)-3-methylbutyl]-L-α-aspartyl]-L-phenylalanine 1-methyl ester, N—[N-[3-(3-methoxy-4-hydroxyphenyl)propyl]-L-α-aspartyl]-L-phenylalanine 1-methyl ester, salts thereof, and combinations thereof.

REBIANA is a steviolglycoside from Cargill, which is an extract from the leaves of the Stevia rebaudiana plant (hereinafter referred to as "REBIANA"). This is a crystalline diterpene glycoside, about 300× sweeter than sucrose. Examples of suitable stevioglycosides which may be combined include rebaudioside A, rebaudioside B, rebaudioside C, rebaudioside D, rebaudioside E, rebaudioside F, dulcoside A, dulcoside B, rubusoside, stevioside, or steviolbioside. According to particularly desirable embodiments of the present invention, the combination of high-potency sweeteners comprises rebaudioside A in combination with rebaudioside B, rebaudioside C, rebaudioside F, rebaudioside F, stevioside, steviolbioside, dulcoside A. Sweeteners are generally included in an oral care composition at a level of about 0.0005% to about 2%.

In one embodiment, the sweetener is selected from, REBIANA, NHDC, acesulfame K, and combinations thereof. Additionally, a flavor enhancer such as glucono-δ-lactone can be added to the sweetener composition.

Abrasive Polishing Materials

The compositions of the present invention may comprise from about 6% to about 70%, alternatively from about 10% to about 50%, by weight of the composition, of an abrasive polishing material.

An abrasive polishing material may also be included in the oral compositions. The abrasive polishing material contemplated for use in the compositions of the present invention can be any material that does not excessively abrade dentin. Typical abrasive polishing materials include silicas including gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, rice hull silica, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962. Mixtures of abrasives may also be used. If the oral composition or, particular phase comprises a polyphosphate having an average chain length of about 4 or more, calcium containing abrasives and alumina are not preferred abrasives. The most preferred abrasive is silica.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975. Preferred are the silica xerogels marketed under the trade name "Syloid" by the W.R. Grace & Company, Davison Chemical Division. Also preferred are the precipitated silica materials such as those marketed by the J. M. Huber Corporation under the trade name, "Zeodent", particularly the silica carrying the designation "Zeodent 119." The types of silica dental abrasives useful in the toothpastes of the present invention are described in more detail in Wason, U.S. Pat. No. 4,340,583, issued Jul. 29, 1982. Silica abrasives are also described in Rice, U.S. Pat. Nos. 5,589,160; 5,603,920; 5,651,958; 5,658,553; and 5,716,601.

Anticaries Agents

Another component which can be part of an oral care composition includes anticaries agents. Anticaries agents are generally used in an amount of about 0.01% to about 3.0%, by weight of the composition. It is common to have a fluoride compound present in dentifrices and other oral compositions in an amount sufficient to give a fluoride ion concentration in the composition of from about 0.0025% to about 5.0% by weight to provide anticaries effectiveness. In one embodiment, the fluoride concentration is from about 0.005% to about 2.0% by weight. A wide variety of fluoride ion-yielding materials can be employed as sources of soluble fluoride in the present compositions and methods. Examples of suitable fluoride ion-yielding materials are found in U.S. Pat. No. 3,535,421 to Briner et al. and U.S. Pat. No. 3,678,154 to Widder et al. Representative fluoride ion sources include: stannous fluoride, sodium fluoride, potassium fluoride, amine fluoride, sodium monofluorophosphate, indium fluoride, amine fluorides such as Olaflur, and many others. In one embodiment, the anticaries agent comprises stannous fluoride in an amount of about 0.454%. In another embodiment, the anticaries agent comprises sodium fluoride in an amount of about 0.243%.

Method of Improving Taste of Oral Care Composition

The present invention also relates to methods of improving the taste of an oral care composition by the inclusion of from about 0.0001% to about 1%, by weight of the oral care composition, of a TRPA1 agonist selected from vanillin esters; benzoate esters; hydroxybenzoate derivative; methoxy benzoate derivatives; hydroxybutanedioate derivatives; benzamidobenzoate derivatives; methylpropanoate derivatives; phenyl acetate derivatives; hex-3-enoate derivatives; 2-(furan-2-ylmethylsulfanyl)-3-methylpyrazine; phenylmethoxymethylbenzene; (2R)-2-azaniumyl-3-[(2R)-2-azaniumyl-3-oxido-3-oxopropyl]disulfanylpropanoate; (3E)-2-hydroxy-4,8-dimethylnona-3,7-dienal; (2R)-2-azaniumyl-3-[(2S)-2-azaniumyl-3-oxido-3-oxopropyl]disulfanylpropanoate; (3Z)-3-butylidene-2-benzofuran-1-one; 3-methyl-N-(3-methylbutyl)butan-1-imine; 2-(furan-2-ylmethyldisulfanylmethyl)furan. These materials are discussed more fully above.

Providing an Oral Composition

Such methods include the step of providing an oral care composition comprising an oral care component selected from metal salts, antimicrobial agents, bad breath reduction agents, bleaching agents, surfactants, or a combination thereof. Without being limited by theory, such oral care components are known to create off-tastes in oral care compositions. Such off-tastes may include metallic; soapy; earthy; antibacterial off-tastes; and salty. The oral care compositions and optional components thereof are discussed in more detail above.

Adding the TRPA1 Agonist to the Oral Composition

Such methods further include the step of adding to the oral care composition the TRPA1 agonist.

In one embodiment, the method comprises providing an oral care composition comprising a zinc salt, stannous salt, a potassium salt, copper salt, or a combination thereof; and adding to the oral care composition from about 0.001% to about 0.085% of vanillin isobutyrate, by weight of the oral care composition.

EXAMPLES

Example I

Screening and Selection of TRPA1 Agonists

In order to select TRPA1 agonists that would be preferred for reducing off-tasting chemical components found in oral care compositions, calcium flux receptor activity on the TRPA1 was utilized as the criteria for selection of actives. With allyl isothiocyanate as the TRPA1 positive control, molecules that directly activated the TRPA1 receptor were screened in dimethylsulfoxide (DMSO). Pure molecules of each material were dissolved in DMSO at a concentration of 100 micormolar and then added to an HEK cell line containing the TRPA1 receptor. If they are TRPA1 agonists, they will cause a calcium flux in the cell which fluoresces and may then be measured using a FLIPR machine. The results of such measurement are calculated as calcium counts which are then converted to the figures shown in Table II as a percentage of the control calcium count. Any preincubation figure provided that is higher than 100 means that the material is more active than the control.

TABLE II

TRPA1 Agonist Activity

| | | TRPA1 | |
|---|---|---|---|
| Material | CAS# | Pre-incubation | Direct addition |
| delta-damascone | 57378-68-4 | 138.93 | 0.74 |
| cis-3-Hexenyl cis-3-Hexenoate | 61444-38-0 | 122.24 | −1.04 |
| Benzaldehyde Dimethyl Acetal | 1125-88-8 | 119.85 | −0.68 |
| carvyl acetate | 97-42-7 | 117.9 | −0.25 |
| methyl benzyl butyrate | 3460-44-4 | 116.22 | −0.34 |
| Trans-2-Nonen-1-ol | 31502-14-4 | 115.47 | −0.49 |
| Beta-ionol | 22029-76-1 | 114.23 | −0.01 |
| Geraniol | 106-24-1 | 112.73 | 5.19 |

TABLE II-continued

TRPA1 Agonist Activity

| Material | CAS# | TRPA1 Pre-incubation | TRPA1 Direct addition |
|---|---|---|---|
| Anisyl butyrate | 6963-56-0 | 112.61 | −0.03 |
| ethyl isoeugenol | 7784-67-0 | 111.43 | −0.14 |
| Alpha-Ionone | 127-41-3 | 111.19 | −0.9 |
| Phenethyl salicylate | 87-22-9 | 109.82 | 7.36 |
| 2-phenyl propyl tetrahydrofuran | 3208-40-0 | 108.49 | −0.15 |
| Dihydro-alpha-ionone | 31499-72-6 | 108.18 | 0.11 |
| thymyl methyl ether | 1076-56-8 | 107.74 | −0.16 |
| cis-3-Hexenyl Hexanoate | 31501-11-8 | 105.81 | 0.08 |
| 2,6,6-Trimethyl-1-cyclohexene-1-acetaldehyde | 472-66-2 | 105.76 | −0.32 |
| Ethyl Salicylate | 119.36-8 | 105.75 | −0.53 |
| Propyl 2,4-Decadienoate | 84788-08-9 | 105.2 | −15.66 |
| Carvyl Propionate | 97-45-0 | 105.07 | −0.57 |
| Dihydroeugenol | 2785-87-7 | 103.71 | 0.07 |
| trans-2-Hexenal | 6728-26-3 | 103.19 | 1.62 |
| ethyl vanillin propylene glycol acetal | 68527-76-4 | 103.19 | 0 |
| Piperonyl Acetate | 326-61-4 | 102.49 | −0.28 |
| Maltol | 118-71-8 | 102.4 | −2.79 |
| 2,3-Hexanedione | 3848-24-6 | 101.02 | −0.19 |
| Ethyl Valerate | 539-82-2 | 100.64 | −0.08 |
| Allyl anthranilate | 7493-63-2 | 99.46 | 0.29 |
| Methyl 4-Phenyl butyrate | 2046-17-5 | 98.83 | −0.22 |
| Allyl Butyrate | 2051-78-7 | 97.97 | 0.02 |
| cis-6-Nonen-1-ol | 35854-86-5 | 97.96 | 2.38 |
| Beta-Caryophyllene | 87-44-5 | 97.77 | 0.21 |
| 2,6-Dimethyl-5-Heptenal | 106-72-9 | 97.59 | −0.15 |
| Dihydro-beta-ionol | 3293-47-8 | 97.15 | −0.33 |
| Alpha-Damascone | 43052-87-5 | 96.58 | −2.88 |
| Camphene | 05794-04-7 | 96.51 | −1.43 |
| Lauric Acid | 143-07-7 | 95.97 | −2.82 |
| Isobutyl Acetate | 110-19-0 | 95.69 | −0.23 |
| Acesulfame K | 55589-62-3 | 95.57 | −0.12 |
| Valencene | 04630-07-3 | 94.99 | 0.1 |
| Caffeine | 58-08-2 | 94.64 | −4.08 |
| Sandela | 3407-42-9 | 94.17 | 25.65 |
| Phenylethyl Acetate | 102-20-5 | 93.75 | −22.48 |
| 2-Octanone | 111-13-7 | 93.27 | −17.14 |
| Ethyl Hexanoate | 123-66-0 | 92.3 | 0.41 |
| 3-Phenyl-1-Propanol | 122-97-4 | 92.23 | −0.04 |
| 3,5,5-Trimethyl Hexanal | 3452-97- | 92.18 | 75.68 |
| Sodium Monofluorophosphate | 10163-15-2 | 92 | 0.19 |
| Farmesene | 502-61-4 | 90.8 | −0.32 |
| 2-Pentanone | 107-87-9 | 90.12 | 0.73 |
| Benzaldehyde | 100-52-7 | 90.11 | −1.46 |
| Citronellyl Formate | 105-85-1 | 89.52 | −0.57 |
| 4,5-Dimethyl-3-Hydroxy-2,5-Dihydrofuran-2-one | 28664-35-9 | 89.1 | 0.18 |
| 3-Hexenyl-3-Methylbutanoate | 35154-45-1 | 88.62 | −1.61 |
| Allyl Hexanoate | 123-68-2 | 88.08 | 0.75 |
| Laevo Menthyl Acetate | 16409-45-3 | 87.91 | −9.39 |
| cis-3-Hexenyl Butyrate | 16491-36-4 | 87.89 | −0.46 |
| Octanal | 124-13-0 | 87.89 | −10.98 |
| 5-Methyl-2-Hepten-4-one | 81925-81-7 | 87.8 | 15.5 |
| Guaiacol | 90-05-1 | 87.72 | −0.08 |
| Rhodinol 70 Spec 59508 | 141-25-3 | 87.57 | −9.13 |
| Ethyl Octanoate | 106-32-1 | 87.32 | −0.14 |
| Ethyl Butyrate | 105-54-4 | 87 | −0.32 |
| Alpha-Pinene | 88-56-8 | 86.6 | −3.07 |
| Lauric Aldehyde | 112-54-9 | 85.96 | 19.05 |
| Amyl Alcohol | 71-41-0 | 85.94 | −1.94 |
| Trans-Ferulic Acid | 537-98-4 | 85.61 | −2.53 |
| 4,5,6,7-Tetrahydro-3,6-Dimethylbenzofuran | 494-90-6 | 84.82 | 0.57 |
| 2-Methoxy-3-Methylpyrazine | 2847-30-5 | 84.65 | −0.83 |
| Cinnamic Alcohol | 104-54-1 | 84.02 | −1.45 |
| Kephalis | 36306-87-3 | 83.88 | −0.23 |
| Acetanisole | 100-06-1 | 83.69 | 0.15 |
| Acetoin | 513-86-0 | 82.57 | 0.29 |
| Triethyl Citrate | 77-93-0 | 82.17 | −9.43 |
| Ethyl 2-Methylbutyrate | 7452-79-1 | 81.99 | 0.26 |
| Allyl Cyclohexanepropionate | 2705-87-5 | 81.67 | 0.45 |
| Benzothiazole | 95-16-9 | 81.5 | −2.29 |
| Phenylacetaldehyde Dimethyl Acetal | 101-48-4 | 81.39 | −14.85 |
| 3-Heptanol | 589-82-2 | 81.34 | −1.06 |
| Benzyl Cinnamate | 103-41-3 | 81.11 | −2.39 |
| Acetophenone | 98-86-2 | 81.07 | 0.64 |
| Hexen-1-ol | 928-96-1 | 80.84 | 0.06 |
| M-Dimethoxybenzene | 151-10-0 | 80.56 | −0.59 |
| Rose Oxide Racemic | 16409-43-1 | 80.14 | −6.68 |
| Aspartame | 22839-47-0 | 80.03 | −2.15 |
| 2-Methylundecanal | 110-41-8 | 79.82 | 0.82 |
| Triacetin | 102-76-1 | 79.33 | −17.05 |
| cis-2-nonen-1-ol | 41453-56-9 | 79.2 | −1.09 |
| Ethyl Heptanoate | 106-30-9 | 79.01 | 0.23 |
| L-Tataric Acid | 87-69-4 | 79 | −2.77 |
| Hexyl Propionate | 2448-76-3 | 78.92 | −15.87 |
| Isobutryic Acid | 79-31-2 | 78.64 | 1.15 |
| 2-Ethyl-4-Hydroxy-5-Methyl-3(2)Furanone | 27538-09-6 | 78.56 | −1.06 |
| Citral Dimethyl Acetal | 7549-37-3 | 78.03 | 0.16 |
| 1-(P-Methoxyphenyl)-2-Propanone | 122-84-9 | 77.63 | 0.49 |
| 2-Methyltetrahydrofuran-3-one | 3188-00-9 | 77.52 | −1.5 |
| Ethyl 3-Methyl-3-Phenylglycidate | 77-83-8 | 77.42 | 23.6 |
| 2-Nonanone | 821-55-6 | 77.25 | 0.36 |
| Linalyl Acetate | 115-95-7 | 77.16 | −0.9 |
| 2,3-Diethyl-5-Methylpyrazine | 18138-04-0 | 76.86 | 0.99 |
| 4-Methyl-5-Thiazoleethanol Acetate | 656-53-1 | 76.4 | 0.62 |
| Ethyl Phenylacetate | 101-97-3 | 76.2 | −0.28 |
| Terpinolene | 586-62-9 | 76.18 | −17.21 |
| Amyl Butyrate | 540-18-1 | 75.89 | −2.64 |
| Ethyl Laurate | 106-33-2 | 75.85 | 0.12 |
| Menthyl Acetate | 79-20-9 | 75.78 | −7.24 |
| PEG 300 | | 75.56 | −5.95 |
| Beta Ionone | 14901-07-8 | 75.35 | −2.88 |
| Benzyl Formate | 104-57-4 | 75.31 | −3.01 |
| cis-6-Nonenal | 2277-19-2 | 74.66 | 2.76 |
| Benzyl Acetate | 140-11-4 | 74.45 | −0.31 |
| Amyl 2-Furoate | 1334-82-3 | 74.13 | −2.39 |
| P-Mentha-8-Thiol-3-one | 38462-22-5 | 73.82 | 46.29 |
| 2-Methyl-2-Pentenoic Acid | 16957-70-3 | 73.79 | −1.27 |
| 2-Methylbutyric Acid | 116-53-0 | 73.68 | −16.66 |
| Beta-Pinene | 127-91-3 | 73.57 | −6.02 |
| 3-(Methylthio) Propanol | 505-10-2 | 73.11 | −0.92 |
| Cuminaldehyde | 122-03-2 | 72.9 | 25.61 |
| Alpha-Methyl-Trans-Cinnamaldehyde | 101-39-3 | 72.88 | 37.95 |
| 4-Methyl-5-Thiazoleethanol | 137-00-8 | 72.77 | 0.56 |
| 5-Ethyl-3-Hydroxy-4-Methyl-2(5H)-Furanone | 698-10-2 | 72.47 | 1.79 |
| Bornyl Isovalerate | 76-50-6 | 72.46 | −1.36 |
| Alpha, Alpha Dimethylphenethyl Acetate | 151-05-3 | 72.03 | −3.2 |
| 4-Hydroxy-2,5-Dimethyl-3(2H)-Furanone | 3658-77-3 | 72 | 2.68 |
| 2-Methyl-1-Butanol | 137-32-6 | 71.64 | −1.19 |
| 2,6-Dimethoxyphenol | 91-10-1 | 71.61 | −0.24 |
| 2-Methoxy-4-Vinylphenol | 7786-61-0 | 71.42 | 1.16 |
| 3-Methylbutyl-2-Methylbutanoate | 27625-35-0 | 71.42 | −1.18 |
| 4-(4-Methoxyphenyl)-2-Butanone | 104-20-1 | 71.31 | −3.93 |
| Roselea Spec 59514 | 04621-04-9 | 71.26 | 14.53 |
| Zinc Oxide | 1314-13-2 | 71.09 | −3.73 |
| Isoamyl Alcohol | 123-51-3 | 70.91 | −0.15 |
| Estragole | 140-67-0 | 70.89 | −0.16 |
| Ethyl Cinnamate | 103-36-6 | 70.82 | 0.45 |
| Alpha-Methylbenzyl Acetate | 93-92-5 | 70.81 | 1.45 |
| Tetrahydrolinalool | 78-69-3 | 70.8 | −17.09 |
| Heptyl Alcohol | 111-70-6 | 70.71 | 0.59 |
| L-Menthone | 89-80-5 | 70.56 | 4.4 |
| Cinnamyl Acetate | 150-84-5 | 70.1 | −0.13 |
| 2-Methylbutyl Isovalerate | 2445-77-4 | 69.9 | −1.49 |
| Allyl Nonanoate | 7493-72-3 | 69.64 | −1.87 |
| Heptanone | 110-43-0 | 69.5 | −0.04 |
| 2 Ethyl-1-Hexanol | 104-76-7 | 69.42 | 0.36 |

TABLE II-continued

TRPA1 Agonist Activity

| Material | CAS# | TRPA1 Pre-incubation | TRPA1 Direct addition |
|---|---|---|---|
| Methyl trans-Cinnamate | 1754-62-7 | 69.38 | −16.79 |
| Phenyl Propyl Acetate | 122-72-5 | 69.3 | −9.54 |
| Furfural | 98-01-1 | 68.97 | −0.15 |
| Cyclohexyl Acetate | 622-45-7 | 68.79 | −1.27 |
| Trans-2-Hexenyl Acetate | 2497-18-9 | 68.67 | −0.32 |
| Acetic Acid | 64-19-7 | 68.53 | 0.27 |
| Jasmonyl | 1322-17-4 | 68.48 | 7.36 |
| 2_Hydroxy-4-Methyl Benzaldehyde | 698-27-1 | 68.24 | 0.4 |
| Ethyl Lactate | 97-64-3 | 67.4 | −0.14 |
| Hexyl Hexanoate | 6378-65-0 | 67.36 | 0.07 |
| Butyl L-Lactate | 3445-19-9 | 67.29 | −0.66 |
| Hexanoic Acid | 142-62-1 | 67.15 | −0.4 |
| Hexyl-2-Methylbutyrate | 10032-45-2 | 67.14 | −0.38 |
| 2,5-Dimethylpyrazine | 123-32-0 | 66.82 | −1.08 |
| Rhodinyl Acetate | 141-11-7 | 66.4 | −17.14 |
| 3-Methyl-2-Butenal | 1115-11-3 | 66.3 | 34.43 |
| Hexyl Alcohol | 111-27-3 | 66.24 | −0.22 |
| Butyraldehyde | 123-72-8 | 66.22 | 28.94 |
| Benzyl Ethyl Ether | 539-30-0 | 66.22 | −2.24 |
| 2-Undecanone | 112-12-9 | 65.88 | 10.65 |
| L-Linalool | 126-91-0 | 65.28 | −11.37 |
| Benzyl Isobutyrate | 103-28-6 | 65.02 | −2.7 |
| Allyl Alpha-Ionone | 79-78-7 | 64.99 | 0.55 |
| ,2,4,5-Trimethythiazole | 13623-11-5 | 64.86 | −1.43 |
| 3-Acetyl-2,5-Dimethylthiophene | 02530-10-1 | 64.38 | 5.75 |
| Phenylethyl Isobutyrate | 103-48-0 | 63.91 | −3.56 |
| Kappa Carrageenan | 09000-07-1 | 63.81 | 0.26 |
| 2-sec-Butylcyclohexanon | 14765-30-1 | 63.73 | −1.47 |
| Ethyl Linalool | 10339-55-6 | 63.35 | −0.1 |
| Linalool Oxide | 1365-19-1 | 63.22 | 0.02 |
| Geranyl Acetate | 105-87-3 | 63.18 | 0.33 |
| Cinnamic Acid | 621-82-9 | 63.08 | −1.66 |
| 4-P-hydroxyphenyl-2-butanone | 5471-51-2 | 63.07 | 0.2 |
| Benzyl Propionate | 122-63-4 | 63.02 | 0.52 |
| Ethyl Isovalerate | 108-64-5 | 62.76 | −0.05 |
| 2,3-Dimethylpyrazine | 5910-89-4 | 62.63 | −1.77 |
| Salicylaldehyde | 90-02-8 | 62.52 | 0.01 |
| Saccharin Sodium | 128-44-9 | 62.52 | −12.39 |
| Polyethylene glycol | 25322-68-3 | 62.47 | 0.58 |
| 2-Ethyl-4-Methythiazole | 15679-12-6 | 62.39 | −1.38 |
| Butyl Butyrate | 109-21-7 | 62.33 | −0.66 |
| Ethyl Anthrailate | 87-25-2 | 61.95 | 39.71 |
| Gamma-Terpinene | 99-85-4 | 61.49 | 0.21 |
| Geranyl Butyrate | 106-29-6 | 61.49 | 0.12 |
| 2-Tridecanone | 593-08-8 | 60.8 | 7.21 |
| Alpha-Terpineol | 98-55-5 | 60.55 | 15.81 |
| P-Totylaldehyde | 104-87-0 | 60.52 | 11.1 |
| (Methylthio)Methylpyrazine | 67952-65-2 | 60.49 | −1.65 |
| Ethyl Benzoate | 93-89-0 | 60.32 | −0.07 |
| 2-Methylbutyl Acetate | 624-41-9 | 60.32 | −0.99 |
| 1-Decanol | 112-30-1 | 59.75 | −1.41 |
| Isoamyl Isovalerate | 659-70-1 | 59.59 | 0.18 |
| Fenchyl Acetate | 13851-11-1 | 59.08 | −0.1 |
| Benzyl Butyrate | 103-37-7 | 58.68 | −3.01 |
| Iso Jasmone | 95-41-0 | 58.16 | 11.48 |
| Magnesium Lactate | 18917-93-6 | 58.12 | −4.49 |
| 2-Aceylthiazole | 24295-03-2 | 57.82 | −1.29 |
| Eugenol benzoate | 531-26-0 | 57.26 | 22.93 |
| Farnesol | 4602-84-0 | 56.63 | 0.1 |
| Benzoin | 119-53-9 | 56.22 | −0.5 |
| Ethyl Methylthio Acetate | 4455-13-4 | 55.69 | −0.06 |
| Tetrasodium Pyrophosphate | 7722-88-5 | 55.35 | −27.8 |
| 2-Octanol | 5978-70-1 | 55.3 | −14.11 |
| Phenyl Ethyl Alcohol | 60-12-8 | 55.03 | −4.77 |
| Zinc Phosphate | 7779-90-0 | 54.62 | 23.15 |
| Stannous Chloride | 7772-99-8 | 54.35 | −14.1 |
| Ethyl-3-Phenylglycinate | 121-39-1 | 54.22 | 12.13 |
| 4-Ethylguaiacol | 2785-89-9 | 53.53 | 55.61 |
| Butyl Propionate | 590-01-2 | 53.41 | −0.32 |
| Isobutyl Hexanoate | 105-79-3 | 53.08 | −17.11 |
| Lactic Acid | 598-82-3 | 53.02 | 34 |
| Phellandrene | 99-83-2 | 52.15 | 1.65 |
| Undecylenic Aldehyde | 112-45-8 | 52.14 | −14.32 |
| Jasmone | 488-10-8 | 51.58 | 46.45 |
| Nonanal | 124-19-6 | 51.43 | −14.01 |
| Cironellol | 106-22-9 | 51.22 | −1.03 |
| Bornyl Acetate | 76-49-3 | 51.18 | −0.6 |
| Borneol | 464.45-9 | 51.05 | −1.6 |
| Gamma Heptalactone | 105-21-5 | 51.03 | 1.18 |
| Gamma-Undecalactone | 104-67-6 | 50.56 | −24.79 |
| Lauryl Alcohol | 112-53-8 | 50.5 | −0.86 |
| 2-Ethylpyrazine | 13925-00-3 | 49.93 | −1.56 |
| Cinnamyl Isovalerate | 140-27-2 | 49.73 | −0.43 |
| Hexyl Acetate | 142-92-7 | 49.15 | −0.01 |
| 2,3,5-Trimethyl-pyrazine | 14667-55-1 | 48.84 | −1.13 |
| Sodium Cyclamate | 139-05-9 | 48.66 | −4.07 |
| Geranyl Propionate | 105-90-8 | 47.94 | 0.09 |
| Linalool | 78-70-5 | 44.84 | −1.58 |
| DL-Menthyl Acetate | 89-48-5 | 43.32 | −16.09 |
| Iso-eugenyl phenylacetate | 120-24-1 | 42.19 | 29.74 |
| Lemarome | 5392-40-5 | 41.41 | 80.13 |
| Isoamyl Acetate | 123-92-2 | 40.98 | 0.07 |
| Butyl Butyryllactate | 7492-70-8 | 39.69 | −1.54 |
| Alpha-Amylcinnamaldehyde | 122-40-7 | 38.15 | −2.55 |
| Ethylene Brassylate | 105-95-3 | 37.24 | −0.58 |
| Phenoxyethyl Isobutyrate | 103-60-0 | 36.8 | −7.84 |
| 2-Methylbutraldehyde | 96-17-3 | 35.61 | 81.04 |
| 1-Benzyloxy-2-Mehtoxy-4-(1-Propenyl) Benzene | 120-11-6 | 30.8 | −3.8 |
| Benzaldehyde Glyceryl Acetal | 1319-88-6 | 30.62 | −2.74 |
| Undecanoic Acid | 112-37-8 | 24.69 | −14.61 |
| Gamma Methyl Ionone | 1335-46-2 | 23.55 | 4.96 |
| Trans-2-Nonenal | 2463-53-8 | 23.31 | 123.46 |
| Zinc Sulfate | 733-02-0 | 21.7 | 29.79 |
| Zinc Acetate | 5970-45-6 | 21.67 | −0.66 |
| Zinc Chloride | 7646-85-7 | 21.61 | 5.46 |
| Allyl Isothiocyanate | 57-06-7 | 21.55 | Control |
| Benzyl Benzoate | 120-51-4 | 18.87 | 53.85 |
| Zinc Oxalate | 094-13-3 | 18.11 | 40.18 |
| 4-Allyl-2,6-Dimethoxyphenol | 6627-88-9 | 15.49 | 39.17 |
| Benzyl Alcohol | 100-51-6 | 14.61 | 21.39 |
| 4-Methyl-2,6-Dimethoxyphenol | 06638-05-7 | 9.25 | 45.88 |
| n-Propyl-4-hydroxybenzoate | 94-13-3 | 8.13 | 173.34 |
| 3-Propylidenephthalide | 17369-59-4 | 6.21 | 116.49 |
| 2-Ethylthiophenol | 4500-58-7 | 5.23 | 0.34 |
| Methyl Anthranilate | 134-20-3 | 1.27 | 69.63 |
| Benzophenone | 119-61-9 | 0 | 138.09 |
| Triclosan | 3380-34-5 | −0.05 | 195.67 |
| Vanillin Isobutyrate | 20665-85-4 | −0.11 | 118.24 |
| Alpha-Amylcinnamaldehyde Dimethyl acetal | 91-87-2 | −0.12 | −2.4 |
| ISO E Super | 54464-57-2 | −0.4 | 11.53 |
| 1-Methylpyrrole-2-carboxaldehyde | 1192-58-1 | −1.04 | −3.47 |
| Citronellyl Oxyacetaldehyde | 7492-67-3 | −1.16 | 147.83 |
| Cinnamaldehyde | 104-55-2 | −1.2 | 114.2 |
| Methyl Ionone | 127-51-5 | −1.32 | 38.43 |
| 6-Methyl-5-Hepten-2-one | 110-93-0 | −1.44 | 0.49 |
| Trans,trans-2,4-Heptadienal | 04313-03-5 | −3.68 | 119.07 |
| trans-2-Heptenal | 18829-55-5 | −3.74 | 95.88 |
| trans,trans-2,4-Undecadienal | 30361-29-6 | −3.93 | 122.12 |
| trans,trans,-2,4-Nonadienal | 5910-87-2 | −4.24 | 112.15 |
| 5-Methyl-2-Phenyl-2-Hexenal | 21834-92-4 | −11.71 | 132.27 |

From the results of the screening shown in Table II, materials were selected based on their expected flavor profile that showed promise as preferable TRPA I agonists. Then, these materials were further screened in Test Formula Ia-Ie, by incorporating at the indicated level. After the toothpaste was made, a small group of panelists (n=4) brushed with the dentifrice and rated the reduction in soapy off taste and the flavor character the compound provided. The results of such screening are shown below in Table III. As seen in Table III, several molecules activated the TRPA1, but only the'vanillin esters provided taste improvements. It is expected that ethyl vanillin isobutyrate will active the TRPA1 receptor similar to vanillin isobutyrate. The vanilla type after taste associated with the vanillin esters further enables these molecules to provide a positive taste improvement and indicates that these molecules act on taste receptors in addition to the TRPA1 sensate receptors.

Formula I

| Ingredient | Ia | Ib | Ic | Id | Ie |
|---|---|---|---|---|---|
| Cocamidopropyl Betaine (30%) | 3.3 | 3.3 | 3.3 | 3.3 | 3.3 |
| Xanthan gum | 0.2 | 0.2 | 0.2 | 0.2 | 0.2 |
| Sodium Fluoride | 0.243 | 0.243 | 0.243 | 0.243 | 0.243 |
| Sodium Hydroxide (50%) | 2.0 | 2.0 | 2.0 | 2.0 | 2.0 |
| Sorbitol (70%) | 44 | 44 | 44 | 44 | 44 |
| Sodium Saccharin | 0.4 | 0.4 | 0.4 | 0.4 | 0.4 |
| Polyethylene Oxide MW 2,000,000 | 0.2 | 0.2 | 0.2 | 0.2 | 0.2 |
| Carbomer 956 | 0.3 | 0.3 | 0.3 | 0.3 | 0.3 |
| Sodium Carboxymethylcellulose | 0.8 | 0.8 | 0.8 | 0.8 | 0.8 |

-continued

Formula I

| Ingredient | Ia | Ib | Ic | Id | Ie |
|---|---|---|---|---|---|
| Sodium acid pyrophosphate | 2.0 | 2.0 | 2.0 | 2.0 | 2.0 |
| Titanium Dioxide, Anatase | 0.2 | 0.2 | 0.2 | 0.2 | 0.2 |
| Hydrated Thickening Silica | 5.0 | 5.0 | 5.0 | 5.0 | 5.0 |
| Hydrated abrasive Silica amorphous | 17 | 17 | 17 | 17 | 17 |
| Monoalkyl Phosphate (30%) | 3.0 | 3.0 | 3.0 | 3.0 | 3.0 |
| Peppermint Flavor | 1.0 | 1.0 | 1.0 | 1.0 | 1.0 |
| Triclosan | 0.05 | — | — | — | — |
| Vanillin Isobutyrate | — | 0.02 | — | — | — |
| Ethyl vanillin isobutyrate | — | — | 0.02 | — | — |
| 4-Methyl-2-phenyl-2-hexenal | — | — | — | 0.06 | — |
| Benzophenone | — | — | — | — | 0.015 |
| Water | QS | QS | QS | QS | QS |

TABLE III

Molecules Screened in Formulation Ia-Ie

| Molecule | CAS#/FEMA# | Structure | % of AITC Receptor Activation (from Data in Table II) | Qualitative Team Evaluations (n = 4) |
|---|---|---|---|---|
| Triclosan | 3380-34-5 | 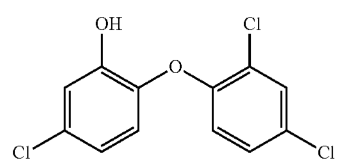 [SMILES: Oc1cc(Cl)ccc1Oc1ccc(Cl)cc1Cl] | 277% | Shifted off-taste from soapy to bitter after 10 minutes |
| Benzophenone | 119-61-9 2134 | 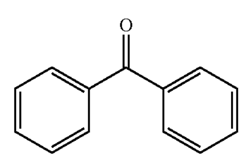 [SMILES: O=C(c1ccccc1)c1ccccc1] | 138% | No observable effect |
| 4-Methyl-2-phenyl-2-hexenal | 26643-92-5 4194 | 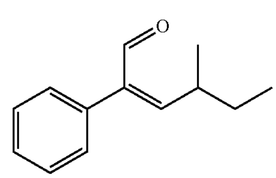 | 132% | Reduces the bitterness from alkyl phosphates, but it has a bitter character on its own |
| Vanillin Isobutyrate | 20665-85-4 3754 | 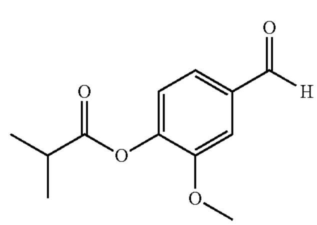 [SMILES: COc1cc(C=O)ccc1OC(=O)C(C)C] | 118% | Great reduction in bitter taste with no aftertaste. Slight vanilla character. |

TABLE III-continued

Molecules Screened in Formulation Ia-Ie

| Molecule | CAS#/ FEMA# | Structure | % of AITC Receptor Activation (from Data in Table II) | Qualitative Team Evaluations (n = 4) |
|---|---|---|---|---|
| Ethyl vanillin isobutyrate | 188417-26-7 3837 | 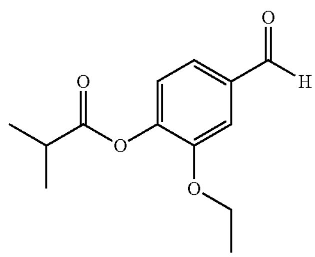 [SMILES: CCOc1cc(C=O)ccc1OC(=O)C(C)C] | Structural analog of Vanillin isobutyrate | Great reduction in bitter taste with no aftertaste. Slight vanilla character. Similar to vanillin isobutyrate |
| AITC | 57-06-7 2477 | 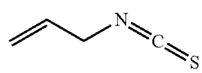 | 100% | Control for receptor testing |

Example II

Oral Care Compositions

Oral care compositions according to the present invention are made by conventional methods and are exemplified below as formulations IIa through IIi.

| Ingredient | IIa | IIb | IIc | IId | IIe | IIf | IIg | IIh | IIi |
|---|---|---|---|---|---|---|---|---|---|
| Carbomer 956 | 0.2 | | | 0.3 | 0.2 | 0.2 | 0.2 | 0.2 | 0.2 |
| CMC | | 0.75 | 0.2 | | | 1.0 | 1.0 | 1.0 | 1.0 |
| Color Solution (1%) | 0.05 | 0.05 | 0.50 | 0.75 | 0.18 | 0.02 | 0.25 | 0.05 | 0.05 |
| Wintergreen Spice Flavor | | | | | 0.15 | | | | |
| Fruit Mint Flavor | | 0.55 | | | | | | | |
| Mint Flavor | 0.59 | | 0.45 | | 0.42 | 1.0 | 1.2 | 1.0 | 1.0 |
| Cinnamon Flavor | | | | 0.5 | | | | | |
| Vanillin Isobutyrate | | 0.01 | | 0.04 | 0.06 | | | 0.03 | 0.05 |
| Vanillyl Butyl Ether | | | | | 0.02 | | | | |
| WS-23 | | | 0.02 | 0.05 | 0.02 | | | | |
| WS-3 | | | 0.02 | 0.05 | 0.02 | | | | |
| MGA | | | | 0.2 | | | | | |
| Menthol | 0.52 | 0.55 | 0.56 | 0.15 | 0.58 | | | | |
| Evercool 180 | 0.01 | 0.03 | 0.015 | 0.004 | 0.01 | 0.01 | 0.03 | 0.008 | 0.02 |
| Potassium Sorbate | | | | | | 0.004 | 0.008 | 0.004 | 0.004 |
| Poloxamer 407 | | | 1.0 | | 0.2 | 0.2 | 0.2 | 0.2 | 0.2 |
| Polyethylene Glycol 300 | 3.0 | 3.0 | | 3.00 | | | | | |
| Polyethylene Glycol 600 | | | 2.3 | | | | | | |
| Propylene Glycol | | | 10.0 | | | | | | |
| Sweetener | 0.46 | 0.5 | 0.45 | 0.4 | 0.58 | 0.4 | 0.4 | 0.4 | 0.4 |
| Silica Abrasive | 22.0 | 31.0 | 20.0 | 21.0 | 17.0 | 15.0 | 15.0 | 15.0 | 15.0 |
| Sodium Benzoate | | | | | | 0.004 | 0.004 | 0.004 | 0.004 |
| Silica Thickening | | | 2.0 | | | 7.0 | 7.0 | 7.0 | 7.0 |
| Sodium Bicarbonate | | 1.50 | 9.0 | | | | | | |
| Sodium Carbonate | | 0.50 | | | | | | | |
| NaOH 50% Soln | | | 1.74 | 2.20 | | 2.0 | 2.0 | 2.0 | 2.0 |
| Na Lauryl Sulfate (27.9% soln) | 4.0 | 5.0 | 3.0 | 4.0 | 4.0 | | | 3.0 | 2.0 |
| Sodium Fluoride | | | | | | 0.243 | 0.243 | 0.243 | |
| Sodium MFP | 0.76 | 0.76 | 0.76 | 0.76 | 0.76 | | | | 0.76 |
| Glycerin USP 99.7% | 9.0 | 11.9 | 33.0 | 9.0 | | | | | |
| Sorbitol Soln USP | 24.3 | 24.5 | 4.0 | 44.7 | 56.9 | 43.0 | 43.0 | 40.0 | 38.0 |

-continued

| Ingredient | IIa | IIb | IIc | IId | IIe | IIf | IIg | IIh | IIi |
|---|---|---|---|---|---|---|---|---|---|
| Tetra Na Pyrophosphate, Anhydrous | 2.05 | 5.045 | 3.85 | | 3.85 | | | | |
| Tetra Potassium Pyrophosphate (60% Soln) | 6.38 | | | | | | | | |
| Na Acid Pyrophosphate | 2.1 | | | 4.0 | 1.0 | 4.3 | 4.5 | 4.5 | 2.0 |
| Alkyl Phosphate[1] | | | | | | 3.5 | 6.7 | 3.5 | 3.5 |
| Cocamidopropyl Betaine (30% soln) | | | | | | 3.5 | | | |
| Titanium Dioxide | 0.5 | | 1.0 | | 0.25 | 0.3 | 0.3 | 0.2 | 0.2 |
| TiO$_2$/Carnauba Wax Prills | | 0.6 | | 0.3 | | | | | |
| Xanthan Gum | 0.6 | | 0.4 | 0.45 | 0.7 | 0.3 | 0.3 | 0.3 | 0.3 |
| Water, Purified, USP | QS | QS | QS | QS | QS | QS | QS | QS | QS |

[1]Sodium Laureth Phosphate supplied by Rhodia

Example III

Metal Salt Containing Dentifrice

Dentifrices according to the present invention are made using conventional methods and are shown below as Example formulations IIA-IIIK with amounts in weight %.

| Ingredient | IIIA | IIIB | IIIC | IIID | IIIE |
|---|---|---|---|---|---|
| Calcium Carbonate | | | | 40.00 | |
| Binders | 1.00 | 1.8 | 1.00 | 1.00 | 0.20 |
| Thickeners | 2.00 | 1.00 | 1.25 | 0.4 | 0.8 |
| Color Solution (1%) | 0.05 | 0.05 | | | 0.175 |
| Dibasic Calcium Phosphate Dihydrate | | | 35.00 | | |
| Flavor[1] | 1.00 | 1.00 | 1.00 | 1.00 | 1.00 |
| Coolants | 0.03 | 0.24 | 0.20 | 0.50 | 0.58 |
| Vanillin Isobutyrate | 0.04 | 0.05 | 0.03 | 0.05 | 0.08 |
| VBE | 0.01 | 0.01 | 0.01 | 0.01 | 0.01 |
| Glycerin USP | 16.489 | | 15.00 | | |
| Poloxamer 407 NF | | | | | 0.20 |
| Monosodium Orthophosphate | | | | | |
| Potassium Nitrate | 5.00 | | | | |
| Saccharin Sodium USP | 0.47 | 0.25 | 0.30 | 0.300 | 0.58 |
| Silica Abrasive | 24.00 | 12.50 | | | 17.00 |
| Sodium Lauryl Sulfate (27.9% soln) | 7.50 | 7.00 | 5.50 | 7.00 | 4.00 |
| NaOH 50% Solution | | 1.00 | | | |
| Sodium Monofluorophosphate | 0.76 | | 0.76 | 0.76 | 0.76 |
| Sodium Fluoride | | 0.32 | | | |
| Sodium Gluconate | | 1.00 | | | |
| Stannous Chloride Dihydrate | | 1.00 | | | |
| Zinc Citrate | | 0.50 | | | |
| Sodium Phosphate, Tribasic | 3.20 | | | | |
| Humectant | 10.50 | 33.00 | 12.00 | 14.00 | 57.00 |
| Tetra Sodium Pyrophosphate, Anhydrous | | | 0.50 | 0.50 | 3.85 |
| Sodium Acid Pyrophosphate | | | | | 1.00 |
| Titanium Dioxide | 0.50 | 0.50 | | | 0.25 |
| Water, Purified, USP | QS | QS | QS | QS | QS |

| Ingredient | IIIF | IIIG | IIIH | III | IIIK |
|---|---|---|---|---|---|
| Calcium Carbonate | | | | 40.00 | |
| Binders | 1.00 | 1.8 | 1.00 | 1.00 | 0.20 |
| Thickeners | 0.5 | 1.00 | 1.25 | 0.4 | 0.8 |
| Color Solution (1%) | 0.05 | 0.05 | | | 0.175 |
| Dibasic Calcium Phosphate Dihydrate | | | 35.00 | | |
| Flavor[1] | 1.5 | 1.0 | 0.8 | 1.00 | 0.8 |
| Coolants | 0.5 | 0.2 | | 0.08 | |
| Glycerin USP | 16.489 | | 15.00 | | 0.10 |
| Potassium Nitrate | 5.00 | | | | |
| Vanillin Isobutyrate | 0.08 | 0.05 | 0.09 | 0.03 | 0.05 |
| Sweetener Combinations | 0.47 | 0.25 | 0.30 | 0.300 | 0.58 |
| Silica Abrasive | 24.00 | 12.50 | | | 17.00 |
| Sodium Lauryl Sulfate (27.9% soln) | 7.50 | 7.00 | 5.50 | 7.00 | 4.00 |
| NaOH 50% Solution | | 1.00 | | | |
| Sodium Monofluorophosphate | 0.76 | | 0.76 | 0.76 | 0.76 |
| Sodium Fluoride | | 0.32 | | | |
| Sodium Gluconate | | 1.00 | | | |
| Stannous Chloride Dihydrate | | 1.00 | | | |
| Zinc Citrate | | 0.50 | | | |
| Sodium Phosphate, Tribasic | 3.20 | | | | |
| Humectant | 12.00 | 33.00 | 12.00 | 14.00 | 57.00 |
| Tetra Sodium Pyrophosphate, Anhydrous | | | 0.50 | 0.50 | 3.85 |
| Sodium Acid Pyrophosphate | | | | | 1.00 |
| Titanium Dioxide | 0.50 | 0.50 | | | 0.25 |
| Water, Purified, USP | QS | QS | QS | QS | QS |

[1]Flavor comprises about 31.3% menthol supplying about 500 ppm menthol.

Example IV

Mouth Rinse Compositions

Mouth rinse compositions according to the present invention are made using conventional methods and are shown below as Example formulations IVA through IVC with amounts of components in weight %.

| Ingredient | IVA | IVB | IVC |
|---|---|---|---|
| Ethanol, USP 190 proof | 15.000 | 15.000 | 15.000 |
| Glycerin | 7.500 | 7.500 | 7.500 |
| Polysorbate 80, NF | 0.120 | 0.120 | 0.120 |
| Vanillin Isobutyrate | 0.010 | 0.006 | 0.020 |
| Flavor | 0.160 | 0.160 | 0.160 |
| Sweetener Combinations | 0.1 | 0.1 | 0.060 |
| Color Solution | 0.040 | 0.040 | 0.040 |
| Cetylpyridinium Chloride | 0.045 | 0.045 | 0.045 |
| Benzoic Acid | 0.005 | 0.005 | 0.005 |
| Sodium Benzoate | 0.054 | 0.054 | 0.054 |
| Water | QS | QS | QS |

Example V

Peroxide Mouth Rinse Compositions

Peroxide-containing mouth rinse compositions according to the present invention are shown below as Example formulations VA through VF, with amounts of components in weight %. These compositions are made using conventional methods. The mouth rinse compositions provide a pleasant high-impact minty taste during use and noticeable long-lasting fresh breath.

| Ingredient | VA | VB | VC | VD | VE | VF |
|---|---|---|---|---|---|---|
| 35% $H_2O_2$ solution | 4.286 | 4.286 | 4.286 | 2.143 | 4.286 | 4.286 |
| Coolant | 0.075 | 0.02 | 0.04 | 0.04 | 0.03 | 0.04 |
| Flavor | 0.145 | 0.135 | 0.135 | 0.15 | 0.135 | 0.135 |
| Vanillin Isobutyrate | 0.025 | 0.030 | 0.025 | 0.02 | 0.015 | 0.010 |
| Poloxamer 407 | 0.75 | 0.75 | 0.750 | 0.10 | 0.10 | 0.10 |
| Glycerin | 11.00 | 11.00 | 11.00 | 20.00 | 20.00 | 20.00 |
| Propylene Glycol | 3.00 | 3.00 | | 4.00 | 4.00 | 4.00 |
| Sweetener Combinations | 0.08 | — | 0.068 | 0.06 | 0.08 | 0.06 |
| Polyphosphate | | | 1.00 | | | |
| Phytic Acid | | 2.00 | | | | |
| Cetyl Pyridinium Chloride | | | | 0.074 | 0.10 | 0.10 |
| Na Citrate | 0.212 | 0.212 | | | | |
| Citric Acid | 0.052 | 0.052 | 0.052 | | | |
| Alcohol, USP | | | 5.00 | | | |
| Water, Purified, USP | QS | QS | QS | QS | QS | QS |

Example VI

Tartar Control Dentifrice Compositions

Tartar control dentifrice compositions according to the present invention are made using conventional methods and are shown below as Examples VIA through VIE with amounts in weight %.

| Ingredient | VIA | VIB | VIC | VID | VIE |
|---|---|---|---|---|---|
| Calcium Peroxide FCC | | | 0.10 | | |
| Thickener | 5.0 | 2.5 | 4.5 | 0.80 | 5.0 |
| Binder | 0.60 | 0.75 | 0.40 | 0.45 | 0.70 |
| Polymer | | | 0.20 | | |
| Color Solution (1%) | 0.05 | 0.05 | 0.50 | 0.75 | 0.175 |
| Flavor | | | | | 0.15 |
| Coolant | | | 0.02 | 0.05 | 0.02 |
| Glycerin USP 99.7% | 9.00 | 11.85 | 33.164 | 9.00 | |
| Poloxamer 407 NF | | | 1.00 | | 0.20 |
| Vanillin Isobutyrate | 0.06 | 0.03 | 0.08 | 0.02 | 0.06 |
| Tetra Potassium Pyrophosphate (60% Soln) | 6.38 | | | | |
| Propylene Glycol USP Crest | | | 10.00 | | |
| Sweetener Combinations | 0.46 | 0.50 | 0.45 | 0.40 | 0.58 |
| Sodium Acid Pyrophosphate | 2.10 | | | 4.00 | 1.00 |
| Silica Abrasive | 22.00 | 31.00 | 20.00 | 21.00 | 17.00 |
| Silica Thickening | | | 2.00 | | |
| Sodium Bicarbonate USP | | 1.50 | 9.00 | | |
| Sodium Carbonate Anhydrous NF | | 0.50 | | | |
| Sodium Hydroxide 50% Solution | | 1.74 | 2.20 | | |
| Sodium Lauryl Sulfate (27.9% soln) | 4.00 | 5.00 | 3.00 | 4.00 | 4.00 |
| Sodium Monofluorophosphate | 0.76 | 0.76 | 0.76 | 0.76 | 0.76 |
| Sorbitol Solution USP | 24.28 | 24.54 | 3.985 | 44.686 | 56.885 |
| Tetra Sodium Pyrophosphate, Anhydrous | 2.05 | 5.045 | 3.85 | | 3.85 |
| Titanium Dioxide | 0.50 | | 1.00 | | 0.25 |
| Titanium Dioxide/Carnauba Wax Prills | | 0.60 | | 0.30 | |
| Water, Purified, USP | QS | QS | QS | QS | QS |

Example VII

Vanillin Isobutyrate and VBE

To test the ability of a combination of vanillin isobutyrate and vanillyl butyl ether (VBE) to mitigate possible astringency and metallic aftertaste of dentifrice compositions, a dentifrice composition formulated with 0.01% vanillin isobutyrate and 0.01% VBE, by weight of the composition, (sample A) was used by a panel of consumers. For comparison, the same consumers tested a similar formula as sample A that had 0.005% G-180 instead of the vanillin isobutyrate and VBE (sample B), and a similar formula to sample A comprising 0.01% vanillin isobutyrate, 0.01% VBE, and 0.005% G-180 (sample C), in addition to commercially available Crest Complete Extra Fresh (sample D), and commercially available Odol med 3 Original (sample E). Panelists were not told the ingredients of the samples, and the ingredients would not be deducible from general use or analysis, but would require burdensome technical evaluations of the particular formulas. The following table IV shows the results of the consumer test, along with the formulas for samples A-D. As can be seen, sample A, formulated with vanillin isobutyrate and VBE can drive consumer freshness perception. The zinc in formulas A-C was able to be best masked by the vanillin isobutyrate and VBE combination in formulas A and C, as indicated by the higher refreshing taste ratings (66 for A and 67 for C, compared to 52 for B).

TABLE IV (scale 1-100, where 100 is the highest preference score)

| | Sample A | Sample B | Sample C | Sample D | Sample E |
|---|---|---|---|---|---|
| Number of consumers | 313 | 304 | 298 | 302 | 306 |
| Overall Acceptance Rating (scale 1-100) | 58 | 56 | 57 | 60 | 59 |
| Av. Leaving your breath refreshed (scale 1-100) | 67 | 64 | 64 | 65 | 63 |
| Av. Gives long lasting breath freshness (scale 1-100) | 65 | 62 | 62 | 64 | 60 |
| Av. Leaving a feeling of long lasting freshness (scale 1-100) | 65 | 62 | 61 | 63 | 61 |
| Av. refreshing taste (scale 1-100) | 66 | 52 | 67 | 69 | 42 |

Formulas for Table IV

| | A Wt % | B Wt % | C Wt % | D Wt % |
|---|---|---|---|---|
| Stannous Chloride | 0.215 | 0.215 | 0.215 | 0.000 |
| Carbomer 956 | 0.000 | 0.000 | 0.000 | 0.400 |

TABLE IV-continued (scale 1-100, where 100 is the highest preference score)

| | | | | |
|---|---|---|---|---|
| Sodium Fluoride | 0.321 | 0.321 | 0.321 | 0.321 |
| Sorbitol 70% | 40.500 | 40.500 | 40.500 | 20.000 |
| Glycerin | 0.000 | 0.000 | 0.000 | 7.000 |
| Zinc Citrate | 0.788 | 0.788 | 0.788 | 0.000 |
| Sodium Citrate | 0.274 | 0.274 | 0.274 | 0.000 |
| Sodium Saccharin | 0.300 | 0.300 | 0.300 | 0.500 |
| Hydroxyethyl cellulose | 0.300 | 0.300 | 0.300 | 0.300 |
| Sodium CMC | 1.300 | 1.300 | 1.300 | 1.300 |
| Xanthan gum | 0.000 | 0.000 | 0.000 | 0.700 |
| Carrageenan Mixture | 0.700 | 0.700 | 0.700 | 0.000 |
| Disodium pyrophosphate | 0.000 | 0.000 | 0.000 | 1.700 |
| Tetrapotassium pyrophosphate | 0.000 | 0.000 | 0.000 | 7.000 |
| Tetrasodium pyrophosphate | 0.000 | 0.000 | 0.000 | 2.200 |
| Hydrated Silica | 17.000 | 17.000 | 17.000 | 15.000 |
| Sodium Alkyl Sulphate 28% | 5.000 | 5.000 | 5.000 | 5.000 |
| Titanium Dioxide | 0.525 | 0.000 | 0.263 | 0.400 |
| Colorant | 0.113 | 0.000 | 0.057 | 0.300 |
| Blue Pigment | 0.000 | 0.067 | 0.034 | 0.000 |
| Vanillyl Butyl Ether (VBE) | 0.010 | 0.010 | 0.010 | 0.000 |
| Vanillin Isobutyrate | 0.010 | 0.010 | 0.010 | 0.000 |
| Triclosan | 0.000 | 0.000 | 0.000 | 0.280 |
| Coolant (G180) | 0.000 | 0.005 | 0.005 | 0.000 |
| Flavor | 1.000 | 1.000 | 1.000 | 1.000 |
| Water purified | QS | QS | QS | QS |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition having improved taste comprising:
   a. from about 0.05% to about 11% of a metal composition selected from the group consisting of zinc and salts thereof;
   b. from about 0.0001% to about 0.02% TRPA1 agonist wherein the TRPA1 agonist is vanillin isobutyrate; and
   c. from about 0.0001% to about 0.02% warming sensate wherein the warming sensate is vanillyl butyl ether;
      wherein the vanillin isobutyrate and the vanillyl butyl ether reduce a bitter character in the oral care composition;
      and wherein the composition has at most a slight vanilla character.

2. An oral care composition according to claim 1 further comprising a stannous salt selected from the group consisting of stannous fluoride, stannous chloride, stannous iodide, stannous chlorofluoride, stannous actetate, stannous hexafluorozirconate, stannous sulfate, stannous lactate, stannous tartrate, stannous gluconate, stannous citrate, stannous malate, stannous glycinate, stannous pyrophosphate, stannous metaphosphate, stannous oxalate, stannous phosphate, stannous carbonate, and combinations thereof.

3. An oral care composition according to claim 1 wherein the composition further comprises a sweetener selected from sucralose, REBIANA, NHDC, acesulfame K, or a combination thereof.

4. An oral care composition according to claim 1 wherein the composition further comprises from about 0.01% to about 30% of an abrasive.

5. An oral care composition according to claim 1 wherein the composition comprises vanillin isobutyrate and vanillyl butyl ether in about a 1:1 ratio.

6. The oral care composition of claim 1 wherein the composition comprises from about 0.0001% to about 0.01%, by weight of the composition, of the vanillin isobutyrate and from about 0.0001% to about 0.01%, by weight of the composition, of the vanillyl butyl ether.

7. The oral care composition of claim 1 wherein the composition comprises less vanillyl butyl ether than vanillin isobutyrate, by weight.

8. The oral care composition of claim 1 wherein the composition comprises from about 0.05% to about 5%, by weight, of the metal composition.

9. The oral care composition of claim 8 wherein the metal salt comprises zinc citrate.

10. The oral care composition of claim 8 wherein the metal salt comprises zinc lactate.

11. The oral care composition of claim 1 further comprising sodium citrate.

12. The oral care composition of claim 1 further comprising stannous chloride.

13. The oral care composition of claim 1 further comprising hydrated silica.

14. The oral care composition of claim 1 further comprising sodium saccharin.

* * * * *